US005670155A

United States Patent [19]
Kahn

[11] Patent Number: 5,670,155
[45] Date of Patent: Sep. 23, 1997

[54] CONFOMATIONALLY RESTRICTED MIMETICS OF BETA TURNS AND BETA BULGES AND PEPTIDES CONTAINING THE SAME

[75] Inventor: Michael Kahn, Chicago, Ill.

[73] Assignee: Molecumetics, Ltd., Bellevue, Wash.

[21] Appl. No.: 473,401

[22] Filed: Jun. 6, 1995

Related U.S. Application Data

[62] Division of Ser. No. 236,674, May 2, 1994, Pat. No. 5,475,085, which is a continuation of Ser. No. 926,350, Aug. 6, 1992, abandoned, which is a continuation-in-part of Ser. No. 651,800, Feb. 7, 1991, abandoned.

[51] Int. Cl.$^6$ .......................... A61K 39/21; A61K 38/12
[52] U.S. Cl. .......................... 424/208.1; 530/317; 514/11
[58] Field of Search ........................... 530/317; 514/11; 424/208.1

[56] References Cited

U.S. PATENT DOCUMENTS

| | | | |
|---|---|---|---|
| 4,699,898 | 10/1987 | Gottlieb | 514/18 |
| 4,908,203 | 3/1990 | Thornton | 424/86 |

FOREIGN PATENT DOCUMENTS

| | | |
|---|---|---|
| WO 91/05564 | 5/1991 | WIPO . |
| WO 92/20704 | 11/1992 | WIPO . |

OTHER PUBLICATIONS

Kahn, M. et al., "the Incorporation of β–Turn Prosthetic Units Into Merrifield Solid Phase Peptide Synthesis" Tetrahedron Lett. 30, 2317–2320 (1989). see entire article.

Miller, M. et al., "Synthesis of β–Lactams from Substituted Hydroxamic Acids" J. Am. Chem. Soc. 102, 7026–7032 (1980). see entire article.

Kahn and Chen, "Methodology for the Synthesis of Mimetics of Peptide β–turns," Tetrahedron Letters 28(15): 1623–1626, 1987.

Kahn et al., "Nonpeptide Mimetics of β–Turns: A Facile Oxidative Intramolecular Cycloaddition of an Azodicarbonyl System," Journal of the American Chemical Society 110:1638–1639, 1988.

Kahn et al., "The Design and Synthesis of Mimetics of Peptide β–turns," Journal of Molecular Recognition 1(2): 75–79, 1988.

Kahn and Bertenshaw, "The Incorporation of β–Turn Prosthetic Units Into Merrifield Solid Phase Peptide Synthesis," Tetrahedron Letters 30(18): 2317—2320, 1989.

Kahn et al., "The Design and Synthesis of a Nonpeptide Mimic of Erabutoxin," Heterocycles 25: 29–31, 1987.

Kahn and Devens, "The Design and Synthesis of a Nonpeptide Mimic of an Immunosuppressing Peptide," Tetrahedron Letters 27(40): 4841–4844, 1986.

Ball and Alewood, "Conformational Constraints: Nonpeptide β–Turn Mimics," Journal of Molecular Recognition 3(2): 55–64, 1990.

Freidinger et al., "Bioactive Conformation of Luteinizing Hormone–Releasing Hormone: Evidence from a Conformationally Constrained Analog," Science 210: 656–658, 1980.

Kemp and Stites, "A convenient preparation of derivatives of 3(S)–amino–10(R)–carboxy–1,6–diaza–cyclodeca–2,7–dione. The dilactam of L–α, γ–diaminobutyric acid and D–glutamic acid: a β–turn template," Tetrahedron Letters 29(4): 5057–5060, 1988.

Miller et al., "Synthesis of β–Lactams from Substituted Hydroxamic Acids," Journal of American Chemical Society 102:7026–7032, 1980.

Olson et al., "Design and Synthesis of a Protein β–Turn Mimetic," J. Am. Chem. Soc. 112: 323–333, 1990.

Arrhenius and Satterthwait, "The substitution of an amide–amide backbone hydrogen bond in an α–helical peptide with a covalent hydrogen bond mimic," in Proceedings of the American Peptide Symposium, 1990, pp. 870–872.

Carpino et al., "((9–Fluorenylmethyl)oxy)carbonyl (FMOC) Amino Acid Fluorides. Convenient New Peptide Coupling Reagents Applicable to the FMOC/tert–Butyl Strategy for Solution and Solid–Phase Syntheses," J. Am. Chem. Soc. 112: 9651–9652, 1990.

Chang et al., "A Potent Nonpeptide Cholecystokinin Antagonist Selective for Peripheral Tissues Isolated from Aspergillus alliaceus," Science 230: 177–179, 1985.

Chen et al., "Design and synthesis of a CD4 β–turn mimetic that inhibits human immunodeficiency virus envelope glycoprotein gp 120 binding and infection of human lymphocytes," Proc. Natl. Acad. Sci. USA 89: 5872–5976, 1992.

Chipkin et al., "Analgesics," Ann. Rep. Med. Chem. 23: 11–18, 1988.

Corey and Fuchs, "A Synthetic Method for Formyl→Ethynyl Conversion (RCHO→RC≡CH or RC≡CR')," Tetrahedron Lett. 36: 3769–3772, 1972.

Fauchere, J., "Elements for the Rational Design of Peptide Drugs," Adv. in Drug. Res. 15: 29–69, 1986.

Ferreira et al., "Isolation of Bradykinin–Potentiating Peptides from Bothrops jararaca Venom" Biochemistry 9: 2583, 1970.

Gilon et al., "Backbone Cyclization: A New Method for Conferring Conformational Constraint on Peptides," Biopolymers 31: 745–750, 1991.

Goel et al., "N–tert–Butoxycarbonyl–L–Leucinal (Carbamic acid, (1–formyl–3–methylbutyl)–1,1–dimethylethyl ester, (S)–)," Org. Syn. 67: 69–75, 1988.

Gribble and Nutaitis, "Sodium Borohydride in Carboxylic Acid Media. A Review of the Synthetic Utility of Acloxyborohydrides," Org. Prep. Proced. Int. 17: 317–384, 1985.

Hart and Ha, "The Ester Enolate–Imine Condensation Route to β–Lactams," Chem. Rev. 89: 1447–1465, 1989.

(List continued on next page.)

Primary Examiner—Paula K. Hutzell
Assistant Examiner—Benet Prickril
Attorney, Agent, or Firm—Seed and Berry LLP

[57] ABSTRACT

The invention provides materials and methods for synthesizing novel reverse turn mimetics, as well as peptides containing the same. Also provided are novel synthetic nonpeptide therapeutic molecules designed upon the interactions between reverse turn mimetics or peptides containing the same, and receptors, antibodies, or enzymes.

7 Claims, 7 Drawing Sheets

OTHER PUBLICATIONS

Hoffman et al., "The Preparation of 2–Hydrazinyl Esters in High Optical Purity from 2–Sulfonyloxy Esters," *Tetrahedron Letters* 31(21): 2953–2956, 1990.

House and Rasmusson, "Stereoselective Synthesis of α–Substituted α,β–Unsaturated Esters," *J. Org. Chem.* 26: 4278–4281, 1961.

Hruby et al., "Emerging approaches in the molecular design of receptor–selective peptide ligands: conformational, topographical and dynamic considerations," *Biochem. J.* 268: 249–262, 1990.

Hruby, V., "Implications of the X–ray structure of deamino–oxytocin to agonist/antagonist–receptor interactions," *Trends Pharmacol. Sci.* 8: 336–339, 1987.

Krstenansky et al., "A New Approach to Conformationally Restricted Peptide Analogs: Rigid β–Bends. 1. Enkephalin as an Example," *Biochem. Biophys. Res. Commun.* 109(4): 1368–1374, 1982.

Lindlar, H., "Ein Neuer Katalysator für selektive Hydrierungen," *Helv. Chim. Acta* 35(57): 446–450, 1952.

Marshall et al., "Peptide Conformation and Biological Activity," *Ann. Rep. Med. Chem.* 13: 227–238, 1978.

Morgan et al., "Approaches to the Discovery of Non–Peptide Ligands for Peptide Receptors and Peptidases," *Ann. Rep. Med. Chem.* 24: 243–252, 1989.

Rajeswari et al., "A New Synthesis of Amides from Acyl Fluorides and N–Silylamines," *Tetrahedron Letters* 28(43): 5099–5102, 1987.

Römer et al., "An opioid benzodiazepine," *Nature* 298: 759–760, 1982.

Salzmann et al., "A Stereocontrolled Synthesis of (+)–Thienamycin," *J. Am. Chem. Soc.* 102: 6161–6163, 1980.

Sargovi et al., "Design and Synthesis of a Mimetic from an Antibody Complementarity–Determining Region," *Science* 253: 792–793, 1991.

Sasaki and Coy, "Solid Phase Synthesis of Peptides Containing the $CH_2NH$ Peptide Bond Isostere," *Peptides* 8: 119–121, 1987.

Satterthwait et al., "Polypeptides stabilized by covalent hydrogen bond replacements," *Chem. Abst.* 112: 179892y, 1990.

Spatola, A., "Peptide Backbone Modifications: A Structure–Activity Analysis of Peptides Containing Amide Bond Surrogates. Conformational Constraints, and Rela . . . ," in *Chemistry and Biochemistry of Amino Acids, Peptides, and Proteins 7*, Weinstein, Ed., Marcel Dekker, New York, 1983, pp. 276–357.

Valle et al., "Crystal–state structural analysis of two γ–lactam–restricted analogs or Pro–Leu–Gly–$NH_2$," *Int. J. Peptide Protein Res.* 33: 181–190, 1989.

Wasserman et al., "Transamidation Reactions Using β–Lactams. The Synthesis of Homaline," *Tetrahedron Lett.* 23: 465–68, 1982.

Williams et al., "Syntheses and X–ray Crystal Structure Determination of 1,3–Bridged Beta–Lactams," *Journal of the American Chemical Society* 111: 1073–1081, 1989.

CONFOMATIONALLY RESTRICTED MIMETICS OF BETA TURNS AND BETA BULGES AND PEPTIDES CONTAINING THE SAME

CROSS-REFERENCE TO RELATED APPLICATIONS

This application is a division of U.S. Ser. No. 08/236,674 filed May 2, 1994, now U.S. Pat. No. 5,475,085; which is a continuation of U.S. Ser. No. 07/926,350 filed Aug. 6, 1992, now abandoned; which is a continuation-in-part of U.S. Ser. No. 07/651,800 filed Feb. 7, 1991, now abandoned.

GOVERNMENT SUPPORT

Portions of this invention were supported by National Science Foundation Grant CHE-8657046 and National Institute of Health Grant GM-38260. The Government has certain rights to this invention.

BACKGROUND OF THE INVENTION

1. Field of the Invention

This invention relates to peptide mimetics. Peptide mimetics are compositionally well defined, configurationally constrained chemical structures which can serve as surrogates for peptides or proteins in their interactions with receptors, antibodies, and/or enzymes. This invention also relates to a means for three dimensional analysis of specific interactions between peptides and proteins and the complementary regions on receptors, antibodies and enzymes, as well as the development of new therapeutic agents through the use of peptide mimetics.

2. Summary of the Related Art

Peptides and proteins play critical roles in the regulation of all biological processes. Peptides, for example, play a regulatory role as hormones and inhibitors, and are also involved in immunological recognition. The significant biological role of peptides makes important the understanding of the interactions between peptides and their receptors or enzymes to which they bind.

The determination of the receptor bound conformation of a peptide is invaluable for the rational design of peptide analogues. However, Marshall et al., Ann. Rep. Med. Chem. 13:227–238 (1978), discloses that peptides are characteristically highly flexible molecules, the structures of which are strongly influenced by the environment in which they reside. Thus solution structural studies of peptides are not generally useful for determining their receptor-bound conformation.

As no approach is available to predict a priori which new ligand-receptor interactions will lead to antagonists and which will lead to agonists of greater or less potency, it is necessary to perform classical structure-function studies in a systematic way to provide information about the specific amino acid residues and functional groups in a peptide that are important to biological activity. Studies of this nature can utilize conformationally constrained peptide mimetics. For example, Hruby, Trends Pharmacol. Sci. 8:336–339 (1987), suggests that conformational constraints can provide information about the different requirements that a receptor has for a ligand to be an agonist or antagonist.

Generally, peptide mimetics can be defined as structures which serve as appropriate substitutes for peptides in interactions with receptors and enzymes. The development of rational approaches for discovering peptide mimetics is a major goal of medicinal chemistry. Such development has been attempted both by empirical screening approaches and by specific synthetic design.

Screening of pure chemical entities has been of quite limited utility for discovering peptide mimetics. However, Chipkin et al., Ann. Rep. Med. Chem. 23:11 (1988), discloses discovery of ligands for the mu-opioid receptor by this approach; as does Romar et al., Nature 298:760 (1982), for the kappa-opioid receptor.

Screening of complex mixtures of natural products has generally been more successful, especially for the discovery of peptidase inhibitors. For example, Ferreira et al., Biochemistry 9: 2583 (1970), discloses the discovery of the ACE inhibitor, teprotide, by screening the venom of *Bothrops jaraca*. This approach may also be applied to the discovery of receptor ligands. Chang et al., Science 230:177 (1985), discloses the discovery of the CCK antagonist asperlicin, using this approach.

Specific design of peptide mimetics has utilized both peptide backbone modifications and chemical mimics of peptide secondary structure. Spatola, *Chemistry and Biochemistry of Amino Acids, Peptides and Proteins*, Vol. VII (Weinstein, Ed.) Marcel Dekker, New York (1983), p. 267, exhaustively reviews isosteric amide bond mimics which have been introduced into biologically active peptides.

The beta-turn has been implicated as an important site for molecular recognition in many biologically active peptides. Consequently, peptides containing conformationally constrained mimetics of beta-turns are particularly desirable. Such peptides have been produced using either external or internal beta-turn mimetics.

External beta-turn mimetics were the first to be produced. Friedinger et al., Science 210:656–658 (1980), discloses a conformationally constrained nonpeptide beta-turn mimetic monocyclic lactam that can readily be substituted into peptide sequences via its amino and carboxy termini, and that when substituted for $Gly^6$—$Leu^7$ in luteinizing hormone releasing hormone (LHRH), produces a potent agonist of LHRH activity.

Monocyclic lactams have generally been useful as external beta-turn mimetics for studying receptor-peptide interactions. However, the mimetic skeleton in these molecules is external to the beta-turn, which gives rise to numerous limitations. Chief among these is bulkiness, which requires the use of dipeptide mimetics, rather than mimetics of all four residues in an actual beta-turn. Substantial flexibility retained in these beta-turn mimetics makes it unsafe to assume that expected conformations are present, absent considerable conformational analysis. For example, Vallee et al., Int. J. Pept. Prot. Res. 33:181–190 (1989), discloses that a monocyclic lactam beta-turn mimetic did not contain an expected type II' beta-turn in its crystal structure. Another limitation of the monocyclic lactam beta-turn mimetics arises from the difficulty of producing molecules that effectively mimic the side chains of the natural peptide. These difficulties arise from steric hindrance by the mimetic skeleton, which results in a more effective mimic of the peptide backbone than of the side chains. Considering the great importance of side chains in receptor binding, these difficulties strongly limit the versatility of monocyclic lactams.

Although the use of bicyclic lactams reduces problems of flexibility somewhat, conformational analysis of peptides containing these mimetics may still be desirable. Moreover, the side chain hindrance in these molecules may be even worse than that in the monocyclic lactams. Finally, both monocyclic and bicyclic lactams mimic only type II and type II' beta-turns, whereas type I and type III beta-turns are more prevalent in proteins and presumably in peptides.

The limitations presented by external beta-turn mimetics may be minimized by using mimetics in which the mimetic skeleton approximately replaces the space that was occupied by the peptide backbone in the natural beta-turn. Such molecules are known as internal beta-turn mimetics. Internal beta-turn mimetics may not generally reproduce the geometry of the peptide backbone of the particular beta-turn as accurately as external beta-turn mimetics. However, the internal position of the constraint allows replacement of larger sections of peptide, thus making tetrapeptide mimetics possible. The lack of bulk also diminishes the likelihood of steric hindrance of the side chains by the mimetic skeleton.

Internal beta-turn mimetics having biological activity are known in the art. For example, Krstenansky et al., Biochem. Biophys. Commun. 109:1368–1374 (1982), discloses a leucine enkephalin analog in which an internal beta-turn mimetic replaced the residues $Gly^2$—$Gly^3$—$Phe^4$—$Leu^5$, and which acted as an analgesic with one-third the potency of morphine. Other internal beta-turn mimetics have been described.

Kahn et al., Tetrahedron Lett. 27:4841–4844 (1986), discloses an internal beta-turn mimetic, based upon an indolizidinone skeleton, and designed to mimic the lysine and arginine side-chain disposition of the immunosuppressing tripepride Lys—Pro—Arg.

Kahn et al., Heterocycles 25:29–31 (1987), discloses an internal beta-turn mimetic, based upon an indolizidinone skeleton, and designed to correctly position the aspartyl and arginyl side chains of a beta-turn in the proposed bioactive region of erabutoxin.

Kahn et al., Tetrahedron Lett. 28:1623–1626 (1987), discloses a type I beta-turn mimetic which can be incorporated into a peptide via its amino and carboxy termini, and which is designed to mimic an idealized type I beta-turn. See also Kahn et al., J. Am. Chem. Soc. 110:1638–1639 (1988); Kahn et al., J. Mol. Recogn. 1:75–79 (1988).

Similarly, Kemp et al., Tetrahedron Lett. 29:5057–5060 (1988), discloses a type II beta-turn mimetic which can be incorporated into a peptide via its amino and carboxy termini.

Arrhentus et al., 11th Proc. Am. Peptide Symp., Rivier and Marshall, Eds., Escom, Leiden (1990), discloses substitution of an amide-amide backbone hydrogen bond with a covalent hydrogen bond mimic to produce an alpha-helix mimetic.

Diaz et al., Tetrahedron Lett. 32:5725-28 (1991) discloses a method used to prepare conformationally restricted amino acids which are potential nucleators for the formation of antiparallel and parallel beta-sheet structures.

Thus, there have been numerous successes in obtaining mimetics which can force or stabilize peptide secondary structure. However, little success has been reported in incorporating mimetics at the active site of a peptide hormone or neurotransmitter, probably because of the difficulty of producing mimetics that possess appropriately positioned side chain groups. There is, therefore, a need for improved mimetics having greater substituent flexibility to allow for easy synthesis of mimetics having appropriately positioned side chain groups. Moreover, there is a need for improved mimetics having more readily controllable skeletal sizes and angles, so that different types of beta-turn structures can be easily imitated. An ideal mimetic would provide ready control and variation of both side chain positioning and mimetic skeleton size and angles through a modular construction system that allows easy synthesis of a wide variety of mimetics.

For recent reviews of the related art, see Hruby et al., Biochem. J. 268:249–262 (1990); Ball et al., J. Mol. Recogn. 3:55–64 (1990); Morgan et al., Ann. Rep. Med. Chem. 24:243–252 (1989); and Fauchere, Adv. Drug Res. 15:29–69 (1986).

BRIEF SUMMARY OF THE INVENTION

The invention provides materials and methods for the synthesis of reverse turn mimetics. More particularly, the invention provides a modular system for synthesizing reverse turn mimetics having nearly infinite variability in degree of conformational constraint, flexibility, side chain constituents, and in the size and bond angles of the mimetic skeleton. The materials and methods of the invention are readily amenable to incorporation in conventional peptide synthesis procedures.

In a first aspect, the invention provides modular component pieces for the assembly of reverse turn mimetics. In a second aspect, the invention provides solid phase synthesis and liquid phase methods for making reverse turn mimetics and for making peptides containing the same. In a third aspect, the invention provides novel reverse turn mimetics and novel peptide structures containing such reverse turn mimetics. In a fourth aspect the invention provides novel synthetic nonpeptide diagnostic, prophylactic, and therapeutic molecules. In a fifth aspect this invention provides novel methods for determining receptor structure and for identifying agonists and antagonists thereto.

The materials and methods of the invention are useful for probing the molecular interactions between ligands and receptors, antibodies and antigens, enzymes and substrates, and thus for providing therapeutic agonists and antagonists capable of interacting with receptors, antibodies, or enzymes.

Additional preferred embodiments of the invention will be made apparent by the following detailed description, examples, and claims.

DETAILED DESCRIPTION OF THE SPECIFIC EMBODIMENTS

The invention provides a modular system for producing reverse turn mimetics having a virtually limitless range of skeletal sizes and bond angles, and side chain substituents. Reverse turn mimetics according to the invention can thus have alternative side chain substituents without having any changes in the backbone conformation. Moreover, reverse turn mimetics according to the invention possess appropriate termini for incorporation into peptides by standard peptide synthesis procedures. Thus, the invention provides a system for producing a virtually unlimited array of peptides having reverse turn mimetics according to the invention incorporated therein. For purposes of the invention the term "reverse term mimetics" is used in a generic sense, and is intended to encompass mimetics of beta turns, gamma turns, beta hairpins, and beta bulges, all of which are provided by the invention by varying the modular component pieces used.

In a first aspect, the invention provides modular component pieces for the construction of reverse term mimetics. Modular component pieces according to the invention include both L- and D-enantiomeric forms. A first modular component piece according to the invention is characterized by the structural formula

Figure 2:
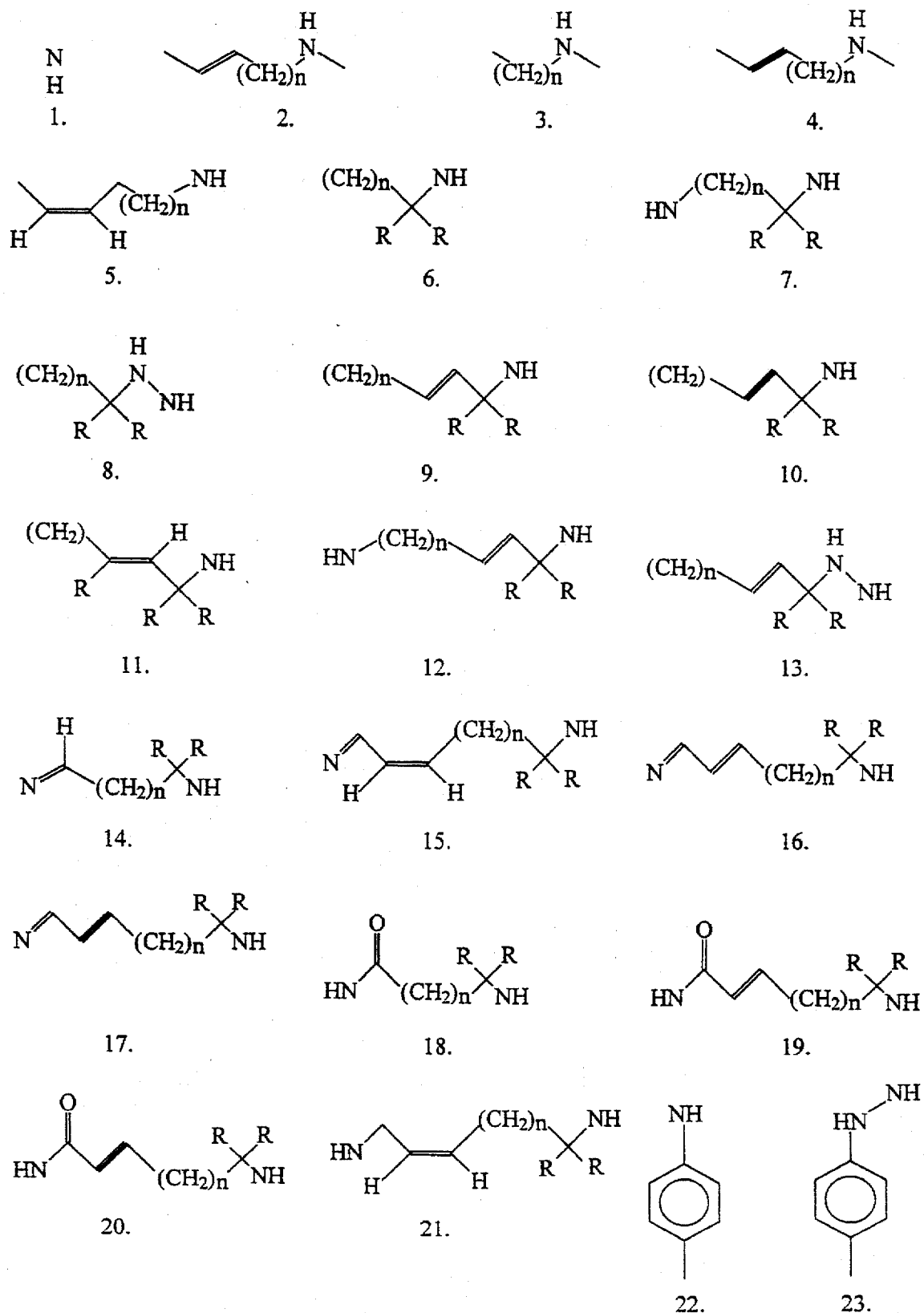
FIG. 2 shows preferred embodiments of the linker moiety, X, of the first modular component piece. For each linker shown, n=0–4 and R=H or $CH_3$. Aromatic linkers are shown in para configuration, but may alternatively be in ortho or meta configuration.

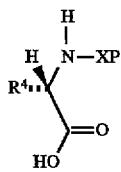

wherein $R^4$ may be any naturally-occurring amino acid side chain substituent, or analog thereof, wherein P is a protective group suitable for use in peptide synthesis, and wherein the linker moiety, X comprises a linker terminating in an amino or hydrazino group, and wherein the termini of the linker are separated by zero to four carbon atoms, and where the carbon atoms involved in carbon-carbon or carbon-nitrogen bonds may be saturated, unsaturated, or aromatic. Specific preferred examples of such linkers are shown in FIG. 2.

The linker group X may be varied in size and or flexibility to control the conformation of the ring in the final mimetic. This allows the construction in a predictable fashion of a nearly infinite variety of conformationally restricted ligands. Ligands having maximum biological activity can then be subjected to spectroscopic and computer-assisted molecular modeling to infer the bound conformation from the determined solution structure.

Such first component piece may be synthesized according to alternative routes, depending on the nature of the X groups. According to a first route, as shown in Example 1, the component is synthesized by the SN2 displacement of an alpha-triflyloxy ester which is readily produced from the corresponding amino acid according to a procedure described by Hoffman and Kim, Tetrahedron Lett. 31:2953 (1990) or by the direct amination method of Vidal, JCS Chem. Comm. 435 (1991).

An alternative route for the synthesis of the first component piece utilizes a quite facile reductive amination reaction, as described by Gribble and Nutaitis, Org. Prep. Proced. Int. 17:317, A85 and Sasaki and Coy, Peptides 8:119 (1987). This method has the advantage of being readily amenable to a large variety of aldehyde components, thus providing a large array of X linker moieties.

A second modular component piece according to the invention comprises an N-protected naturally occurring alpha amino acid or analog thereof which are commercially available or which may be readily synthesized by standard organic synthesis techniques. The second modular component is represented by the structural formula:

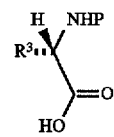

wherein P is a protective group suitable for use in peptide synthesis, and wherein $R^3$ is a naturally-occurring amino acid side chain or analog thereof. A completed mimetic may contain none, one, or two second modular component pieces. When two second modular component pieces are present in a mimetic, the additional R group will be represented in structural formulae as $R^{3'}$.

A third modular component piece according to the invention is characterized by the structural formula:

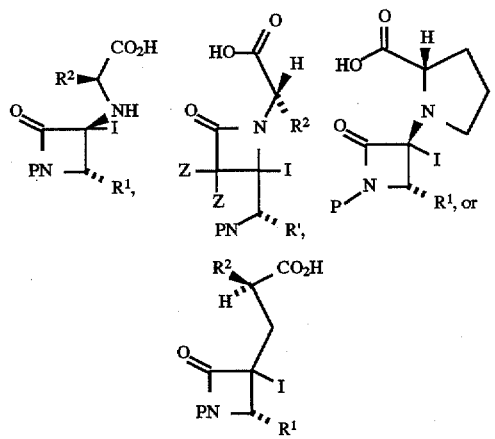

wherein P is a protective group suitable for use in peptide synthesis, wherein Z=H or $CH_3$, and wherein $R^1$ and $R^2$ are naturally-occurring amino acid side chains or analogs thereof and where I is ▶ H or ⋯ H.

A preferred protective group is a tert-butyl dimethylsilyl group.

Such a third modular component piece according to the invention may be synthesized by the route shown in Examples 6–8, which entails selective generation of the ester enolate and condensation with an appropriate N-silylimine, followed by mild hydrolysis. See Hart and Hu, them. Rev. 89:1447. Alternative routes to these third component pieces are outlined in: Salzman et al., J. Am. Chem. Soc. 102:6161 (1980) and; Miller et al., J. Am. Chem. Soc. 102:7026 (1980); Williams et al., J. Amer. Chem. Soc. 111:1073 (1989).

As indicated above, the third modular component piece may be selected from stereoisomers of the same components. The incorporation of stereotsomers of third modular component pieces into the reverse turn mimetics of this invention allows for the synthesis of compounds in a controlled manner, that vary subtly in the orientation of the four R groups; $R_1$, $R_2$, $R_3$ and $R_4$. This provides for access to essentially all potential turn types and allows for detailed mapping of receptor-bound structures.

Figure 1:
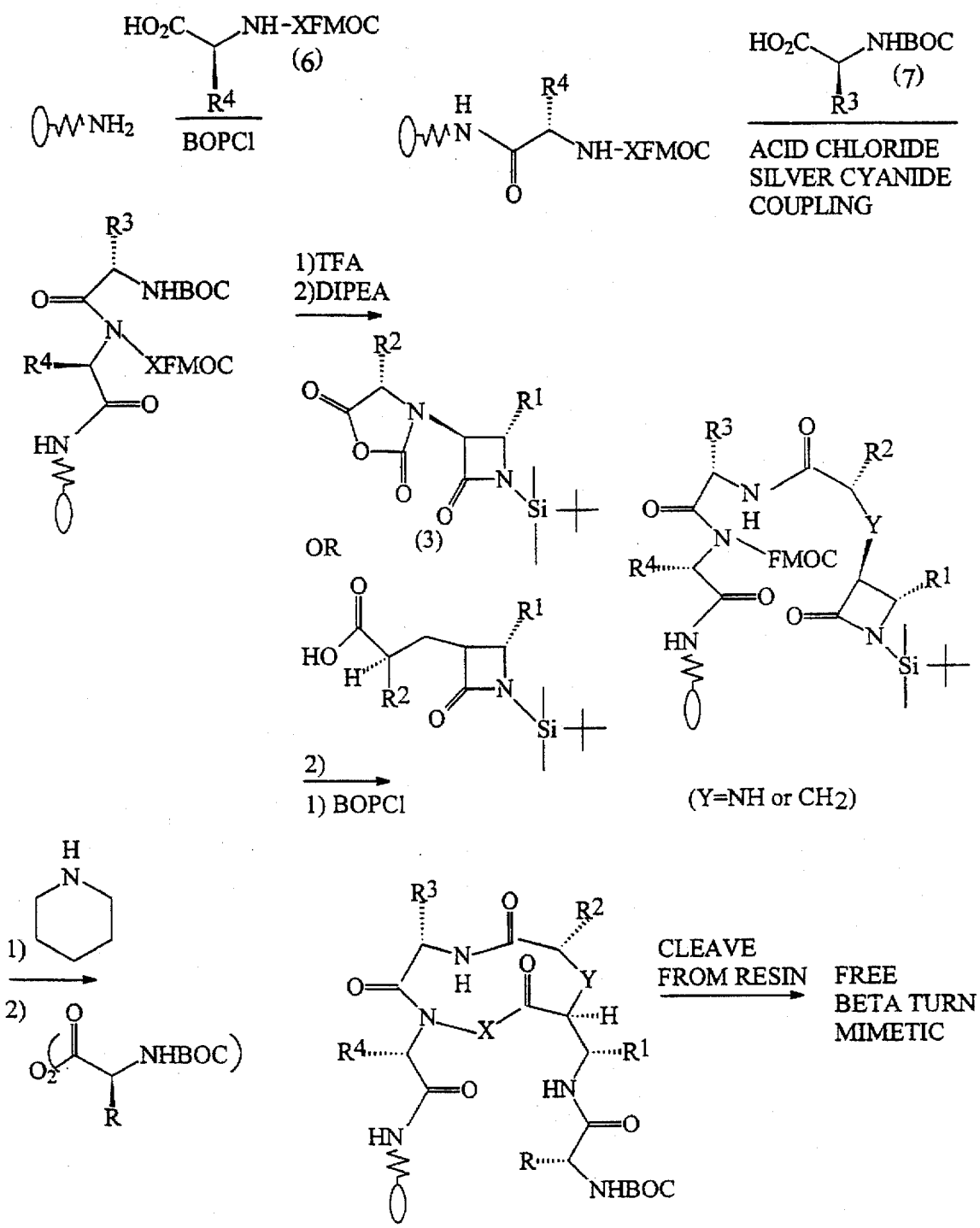
FIGS. 1 and 1A show routes for synthesizing either a reverse turn mimetic according to the invention, or a novel peptide containing the same. The synthesis route shown in FIG. 1 utilizes the modular component pieces of the invention in a standard Merrifield synthesis scheme to produce a reverse turn mimetic. The synthesis route shown in FIG. 1A utilizes the acid fluoride coupling step of this invention to produce a reverse turn mimetic.

In another aspect, the invention provides a method for producing beta-turn mimetics, comprising generally the steps shown in FIG. 1. The synthesis method used may be liquid synthesis or solid phase synthesis. It is preferred, however, that solid phase synthesis be used to take advantage of the ease of purification and rapid production. In order to maximize the benefits of solid phase peptide synthesis it is beneficial to take advantage of the high yields that can be obtained from the silicon mediated acid fluoride coupling of the first modular component piece with the second modular component piece.

A free amino group coupled to a solid support will be the starting point of the solid phase synthesis. The amino group may be coupled to the solid support via a nonpeptide chemical constituent, or it may be the free amino terminus of a nascent peptide being synthesized from the solid support. A first modular component piece according to the invention is then coupled via an amide linkage to the free amino group bound to the solid support, to yield a support-bound first modular component piece.

A second modular component piece according to the invention is then coupled to the support-bound first modular component piece using silicon mediated acid fluoride coupling to yield a support-bound nascent beta-turn mimetic. It has been found that the silicon mediated acid fluoride coupling produces a support-bound intermediate product in excellent yield, with minimal racemization and with a reasonable rate of reaction.

The silicon mediated acid fluoride coupling of a peptide containing an acid fluoride site with a peptide containing a N-silylated bound species results in the formation of a strongly covalent silicon fluoride species by-product allowing the free peptide components to couple. The coupling occurs more efficiently under solid phase synthesis conditions resulting in a high yield of the support-bound nascent reverse turn mimetic.

A mixed anhydride coupling or other type of coupling, such as for example, BOP or anhydride coupling is then carried out between a third modular component piece and the support-bound nascent beta-turn mimetic to yield a support-bound pre-cyclization beta-turn mimetic. The support-bound pre-cyclization beta-turn mimetic is then cyclized to form a support-bound beta-turn mimetic. At this point peptide synthesis maybe continued by adding additional second modular component pieces to the amino acid terminals, or the support-bound structure may be cleaved from the support, or the mimetic can be screened on the resin.

Synthesis of beta-turn mimetics may also be carried out in solution. Synthesis in solution requires essentially the same steps as solid-phase synthesis except that the first modular component piece is not attached to a solid support. Example 15 describes a liquid phase synthesis of a beta-turn mimetic of this invention.

Those skilled in the art will recognize the methods of this invention may be used to synthesize an isolated reverse turn mimetic having variable side chain constituents and backbone size and bond angles, or that it may be readily incorporated into standard Merrifield solid phase peptide synthesis to produce a peptide having such a reverse turn mimetic within it or at either end.

"Reverse turn mimetics" according to the invention actually encompass mimetics of related structures, including gamma turns, beta turns, beta hairpins, and beta bulges. Examples of mimetic gamma turns according to the invention include those represented by the structural formulae:

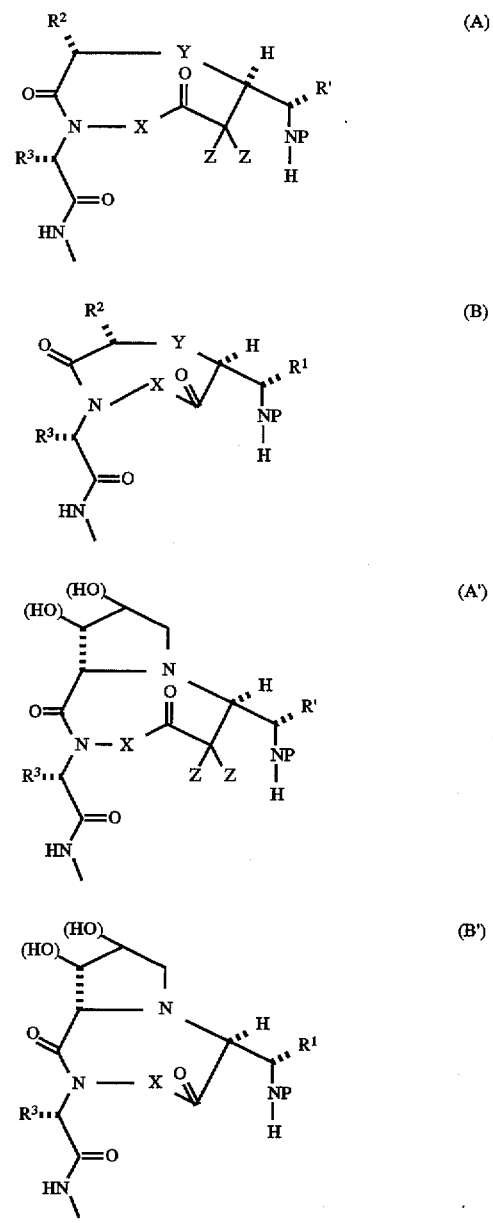

wherein Z=H or CH$_3$, and Y=CH$_2$, NH, or NCH3, and where R$^1$, R$^2$, R$^3$ and R$^4$ is H or naturally occurring or synthetic amino acid side chains or analogs thereof.

Gamma turn mimetics according to the invention are prepared by directly linking together first and third modular component pieces without the use of a second modular component piece. The synthesis of gamma turn mimetics uses the same synthesis techniques described above for preparing beta turn mimetics including coupling a support-bound first modular component piece to a third modular component piece using silicon mediated acid fluoride coupling, Mimetics of actual beta-turns, according to the invention, include those represented by the structural formulae:

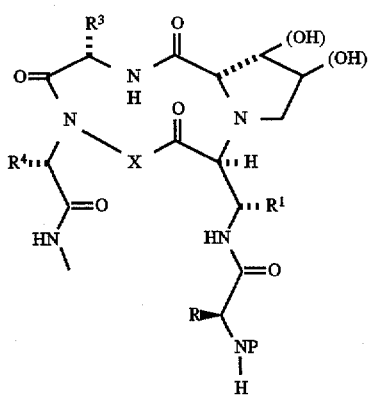

(D')

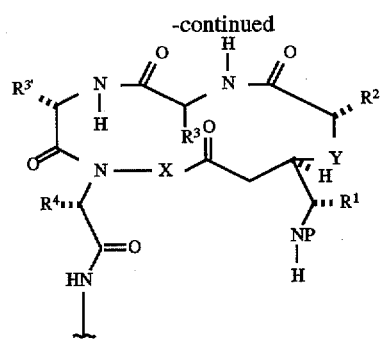

(F)

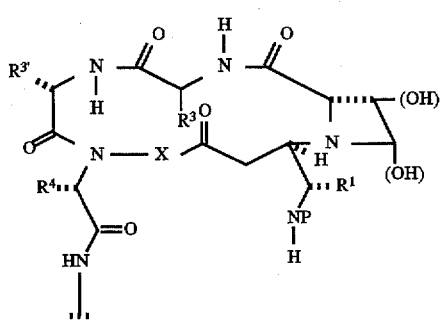

(F')

wherein Y=CH$_2$, NH, or NHCH$_3$, and Z=H or CH$_3$, and R$^1$, R$^2$, R$^3$ and R$^4$ is H or a naturally occurring or synthetic amino acid side chain or analogs thereof.

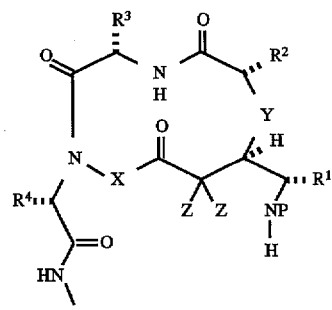

(C)

Beta bulge mimetics according to the invention are prepared by linking two second modular component pieces between the first and third modular component pieces. The synthesis of beta bulge mimetics uses the same synthesis techniques described above for preparing beta turn mimetics including coupling the support-bound first modular component piece to the second modular component piece using silicon mediated acid fluoride coupling.

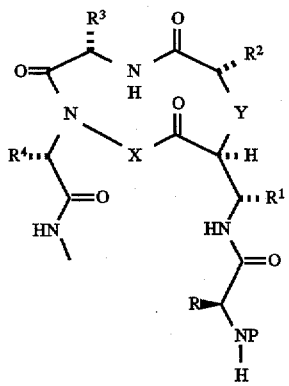

(D)

In all "reverse turn mimetics", according to the invention X—a linker group selected from the group described previously.

Thus, in a third aspect, the invention provides both reverse turn mimetics having variable sizes and bond angles and variable side chain constituents, and peptides containing such reverse turn mimetics internally or at either end. Such reverse turn mimetics, or peptides containing the same, are conformationally restricted, and as such are useful for the design and synthesis of conformationally restricted antigens for making synthetic vaccines or for making antibodies for diagnostic, catalytic or therapeutic purposes.

wherein Y=CH$_2$, NH, or NHCH$_3$, Z=H or CH$_3$ and R, R$^1$, R$^2$, R$^3$, and R$^4$ is H or a naturally occurring or synthetic amino acid side chain or an analog thereof.

Examples of beta bulge mimetics according to the invention include the following structures:

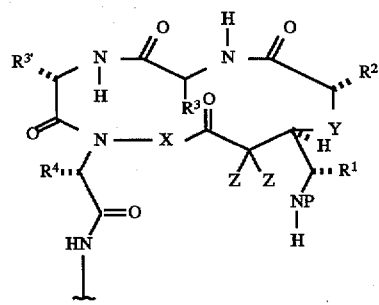

(E)

Synthetic nonpeptide molecules can be produced based upon information obtained from nuclear magnetic resonance (NMR) to determine binding interactions and bound-state conformations of these structures that can be inferred from the solution structure. Molecular modeling can also be employed to interpret the NMR data and to predict improved synthetic nonpeptide structures.

In another aspect, this invention provides various methods for screening and evaluating reverse turn mimetics. Reverse turn mimetics are thought to play critical roles in a number of molecular recognition events. Many occasions arise where either a short linear peptide or short peptide fragment of a protein has shown significant biological activity. However, the determination of the bound structure of that peptide at its receptor is a very difficult task. Due to the multiple low energy conformations that linear peptides may adopt, its solution conformation may not accurately reflect its bound conformation. To overcome this problem a screening method has been developed that uses peptides with conformationally restricted reverse turns mimetics incorporated therein. For example, using a multiple peptide synthesizer (such as the ACT 350) 96 octapeptides can be synthesized with various constraints built in. The following reverse turn mimetics represent a portion of the reverse turn compounds that can be synthesized.

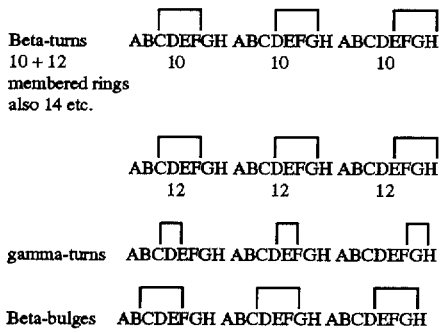

After synthesizing the reverse turn mimetics, they may be assayed in any convenient manner (most preferably in a 96 well ELISA format). Finally, the conformationally constrained peptide which demonstrated maximum biological activity, for example:

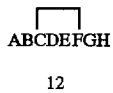

is identified and isolated.

Next, a second round of screening is performed by modifying individual amino acids in the most promising conformationally constrained format identified above with either natural or unnatural amino acids as follows:

etc. These modified peptides are assayed for biological activity. After the most active compound is found, structural analysis using standard techniques (e.g., NMR in conjunction with computer assisted molecular modeling) are used to define the solution conformation, which also represent the bound conformation due to the degree of conformational restriction imposed by the reverse turn mimetic. Thus, in two rounds of synthesis and assaying one can develop a well defined conformationally restricted lead (or therapeutic) compound.

Additional side chain conformational restrictions i.e., dehydro amino acids or gem dimethyl groups can also be incorporated into the compounds to further help define the receptor bound configuration.

An alternative method of screening is used where a novel receptor has been cloned or expressed and the endogenous ligand is unknown, and a receptor agonist or antagonist is sought. A method for determining an agonist or antagonist is to generate a large random library of peptides incorporating conformationally constrained reverse turns and to screen this library with the receptor. A number of groups have developed combinatorial library screening approaches, however for purposes of this invention, a modification of the Houghten (R. A. Houghten, et al., Nature 364:84 (1991)) system is preferred.

The first step in the screening method is to synthesize a dipeptide or a random mixture of dipeptides and divide the dipeptide or mixture thereof into, for example, twenty portions, or "tea bags". Each of the 20 is coupled with a different first modular component. After coupling, the twenty "tea bags" are combined, mixed and then split into 20 tripeptide mixture portions and coupled with 20 different second modular component pieces. At this point there are 400 different combinations coupled to the dipeptide. This process is repeated with a 3rd modular component pieces, e.g.,

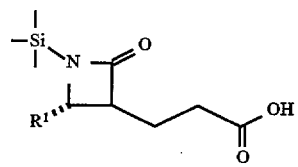

It is preferred that the third modular component piece in the first round of screening have no $R_2$ group in the t+2 position as this is most commonly occupied by Pro or Gly and omitting it simplifies the synthesis. Up to 8,000 different combinatorials attached to the dipeptide or dipeptides have now been produced which are subsequently cyclized to produce reverse turn mimetics of this invention. Finally, one, two or more amino acids can be added onto the N-terminus in a random fashion which will provide millions of combinatorials to screen with the known receptor before or after cleavage from the resin. The peptides which bind with the highest affinity can then be sequenced by FAB MS/MS techniques.

Once a lead component has been identified by one of the above screening techniques, the lead component can be structurally assayed by various techniques including nuclear magnetic resonance (NMR). NMR conformational analysis for small peptide and peptide analog systems in solution is straightforward and well known in the art. For example, see Bax, *Two-Dimensional Nuclear Magnetic Resonance in Liquids*, D. Reidel Publishing Co., Boston, 1982; Wuthrich, *NMR of Proteins and Nucleic Acids*, Wiley-Interscience, New York, 1986; Ernst et al., *Principles of Nuclear MaKnetic Resonance in One and Two Dimensions*, Oxford University Press, New York, 1987.

NMR along with computer-assisted molecular modeling allows the identification of ligand-receptor interactions required for binding. Identifying the interactions required for binding facilitates preparation of synthetic molecules that are capable of similar binding, and therefore of acting as agonists or antagonists. The identification of a stable bound conformation greatly facilitates the preparation of a synthetic therapeutic agent capable of acting as either an agonist or antagonist for one skilled in the art.

Thus, the invention provides synthetic therapeutic molecules capable of acting as agontsts or antagonists, wherein such molecules are based upon structural features of a conformationally restricted reverse turn mimetic that is capable of binding to the receptor. Particularly likely candidates for the development of such therapeutics include synthetic molecules based upon one or more structural features of a binding conformation of a peptide hormone, lymphokine, growth factor, enzyme inhibitor, or vital binding protein.

The following examples are intended to further illustrate the invention, and are not limiting in nature.

EXAMPLE 1

Synthesis of a First Modular Component Piece

First modular component pieces were synthesized according to the following schemes.

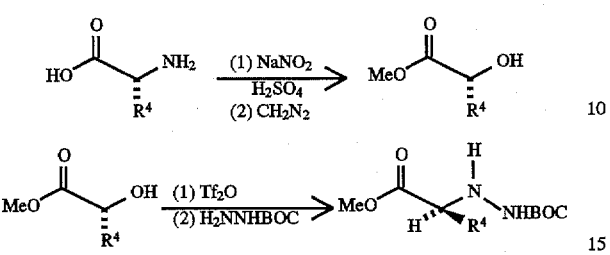

See Hoffman and Kim, Tetrahedron Lett. 31:2953 (1990) and Vidal, JCS Chem. Comm. 435 (1991).

EXAMPLE 2

Examples 2–5 detail various methods for synthesizing linkers of this invention. First modular component pieces of this invention other than those synthesized in Example 1 can be produced from the linkers of Examples 2–5 by a facile reductive amination reaction, as described by Gribble and Nutaitis, Org. Prep. Proced. Int. 17:317, (1985), or Sasaki and Coy, Peptides 8:119 (1987).

Aldehyde Synthesis from Corresponding Carboxylic Acid

Aldehydes were synthesized from their corresponding carboxylic acids according to the following scheme.

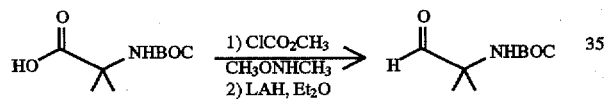

See Goel et al., Org. Syn. 67:69 (1988).

EXAMPLE 3

Wittig Reaction Homologation of Aldehydes

Homologation of aldehydes was carried out using the Wittig reaction, according to the following scheme.

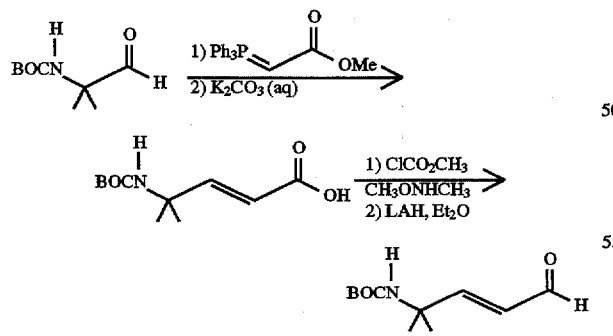

See House and Rasmusson, J. Org. Chem. 26:4278 (1961).

EXAMPLE 4

Alternative Homologation of Aldehydes

Homologation of aldehydes was alternatively carried out according to the following scheme.

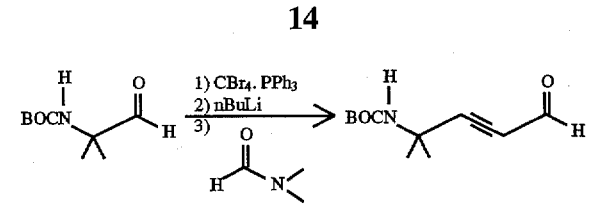

See, Tetrahedron Lett. 13:3769 (1972).

EXAMPLE 5

Preparation of Cis Olefin by Lindlar Reduction of Acetylene

Acetylenes prepared according to Example 4 were used in the Lindlar reduction to prepare cis-isomers.

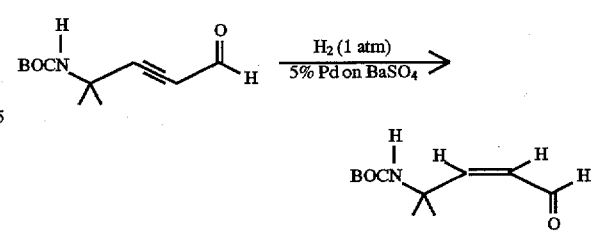

See Lindlar, Helv. Chim. Acta 35:446 (1952).

EXAMPLE 6

Synthesis of Third Modular Component Pieces

Third modular component pieces were synthesized according to the following scheme.

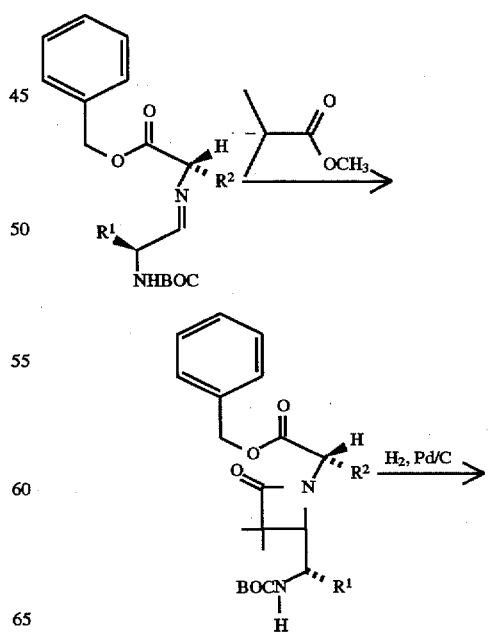

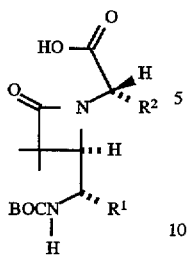

See Hart and Hu, Chem. Rev. 89:1447 (1990). Third modular component pieces synthesized according to this example are used to create mimetics wherein $R^2$ is attached to a carbon atom adjacent to a secondary nitrogen.

EXAMPLE 7

Alternative Synthesis of Third Modular Component Pieces

Third modular component pieces were alternatively synthesized according to the following scheme.

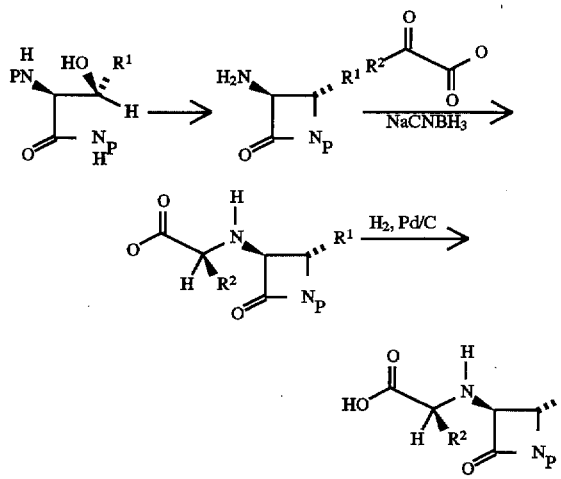

See Miller et al., J. Am. Chem. Soc. 102:7026 (1980). Third modular component pieces synthesized according to this example are use to create mimetics having $R^2$ attached to a carbon atom adjacent to a secondary nitrogen atom.

EXAMPLE 8

Additional Alternative Synthesis of Third Modular Component Pieces

Third modular component pieces were further synthesized according to the following scheme.

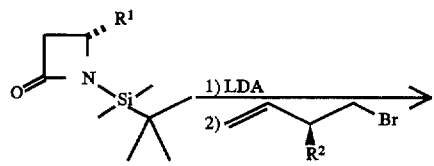

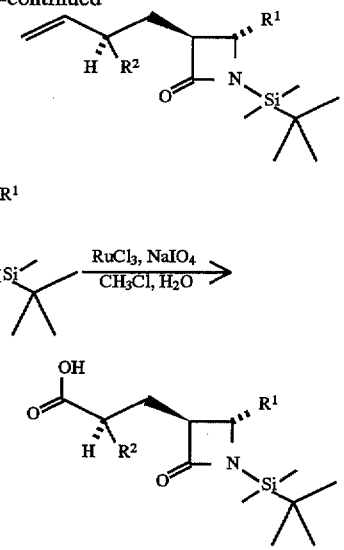

See Williams et al., J. Amer. Chem. Soc. 111:1073 (1989). Third modular component pieces synthesized according to this example are used to create mimetics having $R^2$ attached to a carbon atom adjacent to a carbon atom.

EXAMPLE 9

Preparation of N-t-butyldimethylsilyl-4-(R)-t-butyldimethylilyloxy-2-azetidinone 1

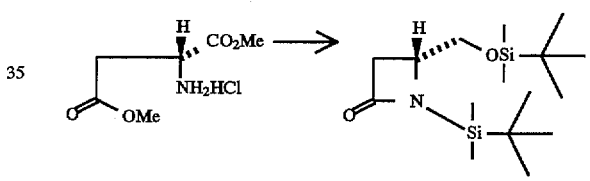

D-aspartic acid dimethylester hydrochloride (2.00 g, 10.1 mmol), t-butyldimethylsilyl chloride (1.68 g, 11.1 mmol) and 4-dimethylaminopyridine (62 mg. 0.51 mmol) were dissolved in 50 ml of methylene chloride. To this mixture was added triethylamine (3.24 ml, 23.3 mmol) at room temperature slowly and the mixture was allowed to stir overnight at room temperature. The mixture was washed with aqueous ammonium chloride, saturated sodium bicarbonate and brine, dried over sodium sulfate and concentrated in vacuo. The residue was dissolved in 50 ml of ether. The solution was cooled to 0° C. and 2.0 M t-butylmagnesium chloride in ether (5.24 ml, 10.5 mmol) was added dropwise. The mixture was allowed to warm to room temperature overnight with stirring and was cooled to 0° C. again. Saturated ammonium chloride was added and the mixture was stirred for 30 min. Water was added to the mixture and the organic layer was separated. The aqueous layer was extracted with ether (2×30 ml). The combined organic extracts were washed with brine, dried over magnesium sulfate and concentrated in vacuo. The residue was dissolved in 60 ml of methanol. To this solution at room temperature, sodium borohydride (1.14 g, 30.1 mmol) was added to a flask equipped with a reflux condenser. The mixture began to reflux during the addition and ceased after 20 min. After 45 min. in total, the mixture was cooled to 0° C. and aqueous ammonium chloride was added. The mixture was extracted with methylene chloride (3×50 ml). The combined organic extracts were dried over sodium sulfate and the volatiles were removed in vacuo. The residue was dissolved in 30 ml of methylene chloride. To this solution was added t-butyl-dimethylsilyl chloride (1.00 g, 6.63 retool) and 4-dimethylamino-pyridine (37 mg, 0.30 mmol). Triethylamine (1.10 ml, 7.87 retool) was added slowly and the mixture was allowed to stir overnight at r.t. The mixture was washed with aqueous ammonium chloride and brine, dried over sodium sulfate and concentrated in vacuo. Flash chromatography of the residue on silica-gel with hexane-ethyl acetate (9/1:v/v) afforded 1.01 g (30%) of 1 as a colorless liquid. H NMR (400 MHz, $CDCl_3$ delta 3.74 (dd, $J_a$=3.96 Hz, $J_b$=10.30 Hz, 1 H), 3.63 (dd, $J_a$=5.12 Hz, $J_b$=10.30 Hz, 1 H), 3.59 (m, 1 H), 3.04 (dd, $J_b$=5.28 Hz, $J_b$=15.22 Hz, 1 H), 2.76 (dd, $J_a$=2.49 Hz, $J_b$=15.22 Hz, 1 H), 0.94 (s, 9 H), 0.88 (s, 9 H), 0.22 (s, 3H), 0.21 (s, 3 H), 0.05 (S, 6 H); $^{13}C$ NMR (100 MHz, $CDCl_3$): delta 172.7 65.3, 50.2, 41.2, 26.2, 25.8, −5.4, −5.5, −5.7.

EXAMPLE 10

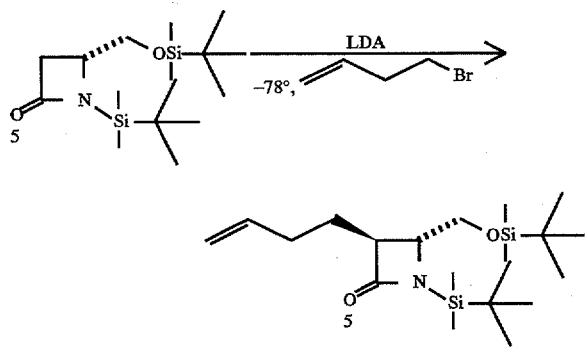

A solution of lithium diisopropyl amide (2.5 mmol in 25 ml of THF) was prepared in the usual manner at 0°. After cooling to −78° C., a solution of azetidinone 5 (323 mg, 1 mmol) in 10 ml of THF was added dropwise and allowed to stir for 30 minutes at −78° C. To this was added 400 ml (4 mmol) of butenyl bromide. Stirring was continued for 18 hr. and the reaction allowed to come to room temperature. The reaction mixture was poured into saturated $NH_4Cl$ solution and extracted 3 times with 50 ml portions of ether, dried over $Na_2SO_4$ and the solvent removed in vacuo. The residue was chromatographed on 15 g of silica gel to provide 294 mg, 78% of azetidinone 6.

EXAMPLE 11

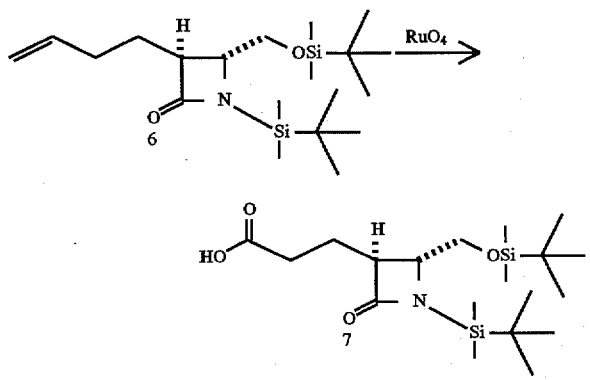

A flask was charged with a magnetic stirrer, $CCl_4$/$CH_3CN$/$H_2O$ (1:1:2, total 4 ml), azetidinone 6 (160 mg, 0.44 mmol) and $NaIO_4$ (469 mg. 2.2 mmol, 5 eq). To this biphasic solution, a catalytic amount of $RuCl_3 \cdot 3H_2O$ was added. The mixture was stirred overnight at room temperature and taken up in ethyl acetate (25 ml) and $H_2O$ (10 ml). The organic layer was separated and the aqueous layer was saturated with sodium chloride (solid) and extracted with ethyl acetate (2×20 ml). The combined organic extracts were dried over $Na_2SO_4$ and concentrated to provide Z, an oil in 55–65% yield and the third modular component piece shown in FIG. 3.

EXAMPLE 12 synthesis of an Inhibitory reverse Turn Mimetic

The azetidinone acid (7) produced in Example 9 (238 mg, 0.59 mmol) was dissolved in 30 ml THF and cooled to 0° C. To this solution was added NMM (147 μl, 2.25 equiv.) and iBuOCOCl (81 μl, 1.05 equiv.) The solution was stirred for 15 minutes at room temperature and then added to a solution of O-benzylserine benzylester (e) (shoe as the second modular component piece in FIG. 3) in 10 ml THF (with 1 equiv. NMM) at 0° C. The reaction was allowed to warm to room temperature and stirred for 12 hours. The reaction was then diluted with 20 ml EtOAc, washed with $NaHCO_3$, brine and $H_2O$ and dried over $Na_2SO_4$. The volatiles were removed in vacuo to provide 176 mg (45% yield) after chromatography on $SiO_2$ 2:1 Hex: EtOAc. The product was dissolved in methanol, a catalytic amount of 10% Pd/C was added and the reaction was placed under 1 atm $H_2$ gas. After 1 hour the reaction was filtered through celite and volatiles were removed in vacuo to provide a quantitative yield of the acid (f) shown in FIG. 3.

Figure 3:
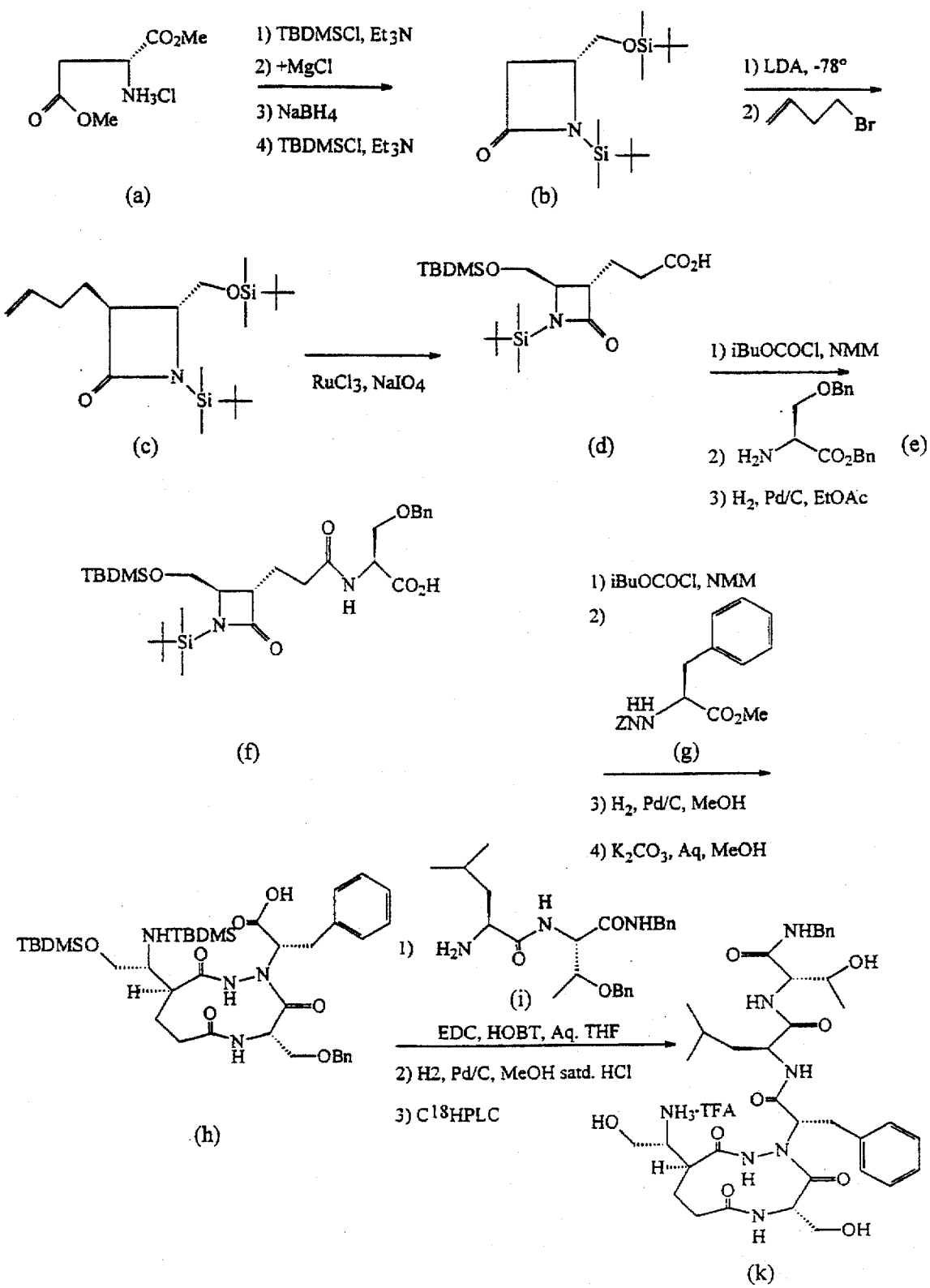
FIG. 3 is a synthetic scheme for a reverse turn mimetic of this invention.

Referring to FIG. 3, to a solution of the azetidinone (f) (116 mg, 0.20 mmol in 2 ml of THF at 0° C.) was added NMM (22 μl, 1 equiv.) and iBuOCOCl (26 μl, 1 equiv.). The reaction was stirred for 15 minutes at room temperature. To this was added a first modular component piece, a solution of the hydrazinophenylalanine derivative (g) (132 mg, 0.40 mmol in 2 ml of $CH_2Cl_2$) (where Z represents a carbobenzyloxy protective group) and the reaction was stirred for 16 hours at room temperature. Column chromatography on silica gel with 50:1 $CH_2Cl$: MeOH as eluent afforded a 37% yield of the precyclization intermediate. Hydrogenolytic deprotection and closure was effected by dissolution in 5 ml MeOH, addition of a catalytic amount of 5% Pd/C and placing of this mixture under 1 arm $H_2$ for 1 hour. Filtration through celite and removal of the volatiles in vacuo provided a nearly quantitative yield of the 10-membered ring methyl ester. The ester was dissolved in 2 ml of 4:1 MeOH:$H_2O$. To this was added 10 mg (1 equiv.) $K_2CO_3$ and the reaction was stirred at room temperature for 16 hours. Removal of the solvent in vacuo provided a quantitative yield of the carboxylic acid as its potassium salt (h).

The carboxylic acid potassium salt (h) (38 mg, 0.05 mmol) was dissolved in 400 μl 1:1 THF:$H_2O$. To this was added EDC (11 mg, 1.1 equiv.), HOBT (7.5 mg, 1.1 equiv.) and the protected dipeptide (i) (45 mg, 0.1 mmol) and the reaction was stirred at room temperature for 24 hours. Removal of the volatiles in vacuo and silica gel chromatography (50:1 $CH_2Cl_2$:MeOH) afforded 62% yield of the protected analog. A solution of this compound in 2 ml MeOH with 1 ml MeOH saturated with HCl and 10 mg 10% Pd/C was placed under 1 arm $H_2$ and stirred at room temperature for 16 hours. Filtration through celite and removal of the volatiles in vacuo afforded 22 mg of gp120 binding inhibitor (60% yield) (mimetic K).

EXAMPLE 13

Assessment of Inhibition of gp120 binding

Figure 4:
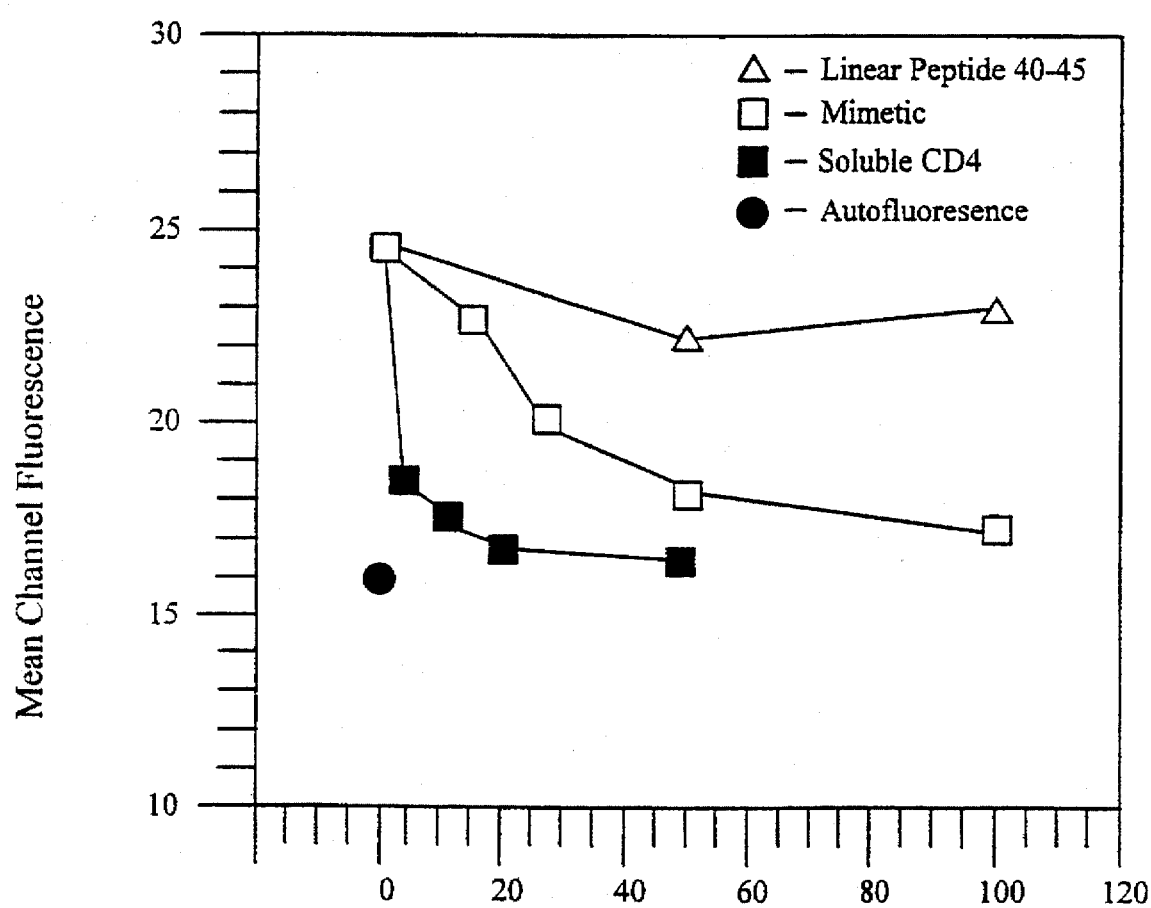
FIG. 4 summarizes data showing inhibition of gp120 binding by soluble CD4 and by a reverse turn mimetic of the invention.

For measuring binding, fluoresceinated gp120 was incubated with mimetic K (See Example 12 or FIG. 5) or with soluble CD4 at 22° C. in binding buffer (Ca²⁺, Mg²⁺ free HBSS, 0.5% BSA, 0.05% sodium azide, pH 7.4). Approximately 300,000 cells (from a 10×10⁷ cell/ml stock) were added to tubes at 4° C. in binding buffer, with a final volume of 100 microliters. Samples were incubated at 4° C. for 40 min. washed in binding buffer and analyzed in FACS immediately. Data was acquired, gating on live cell population (always greater than 90%), and was consistent whether mimetic K, gp120, or other agents were added. Results are shown in FIG. 4. Inhibition by mimetic K was concentration dependent, with an IC$_{50}$ of 0.8 micromolar.

EXAMPLE 14

Inhibition of Syncytium Formation

Figure 5:
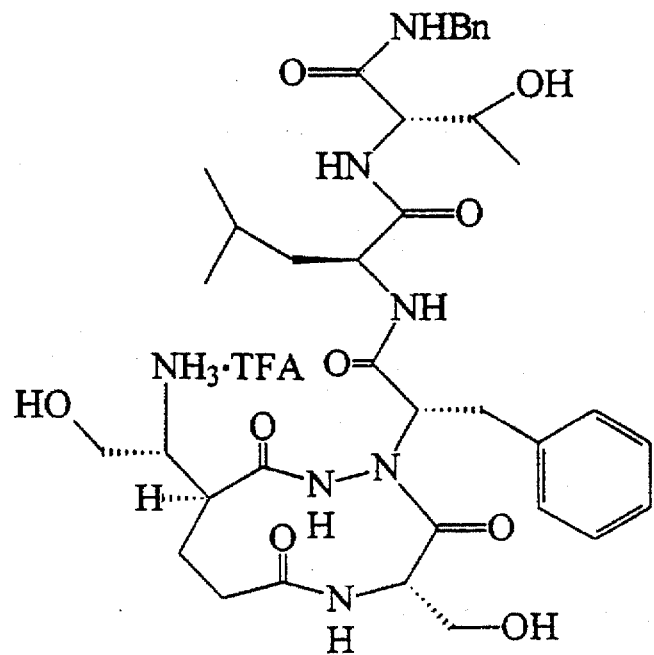
FIG. 5 is a reverse turn mimetic of the full CD4 loop region mimetic structure.
Figure 6:
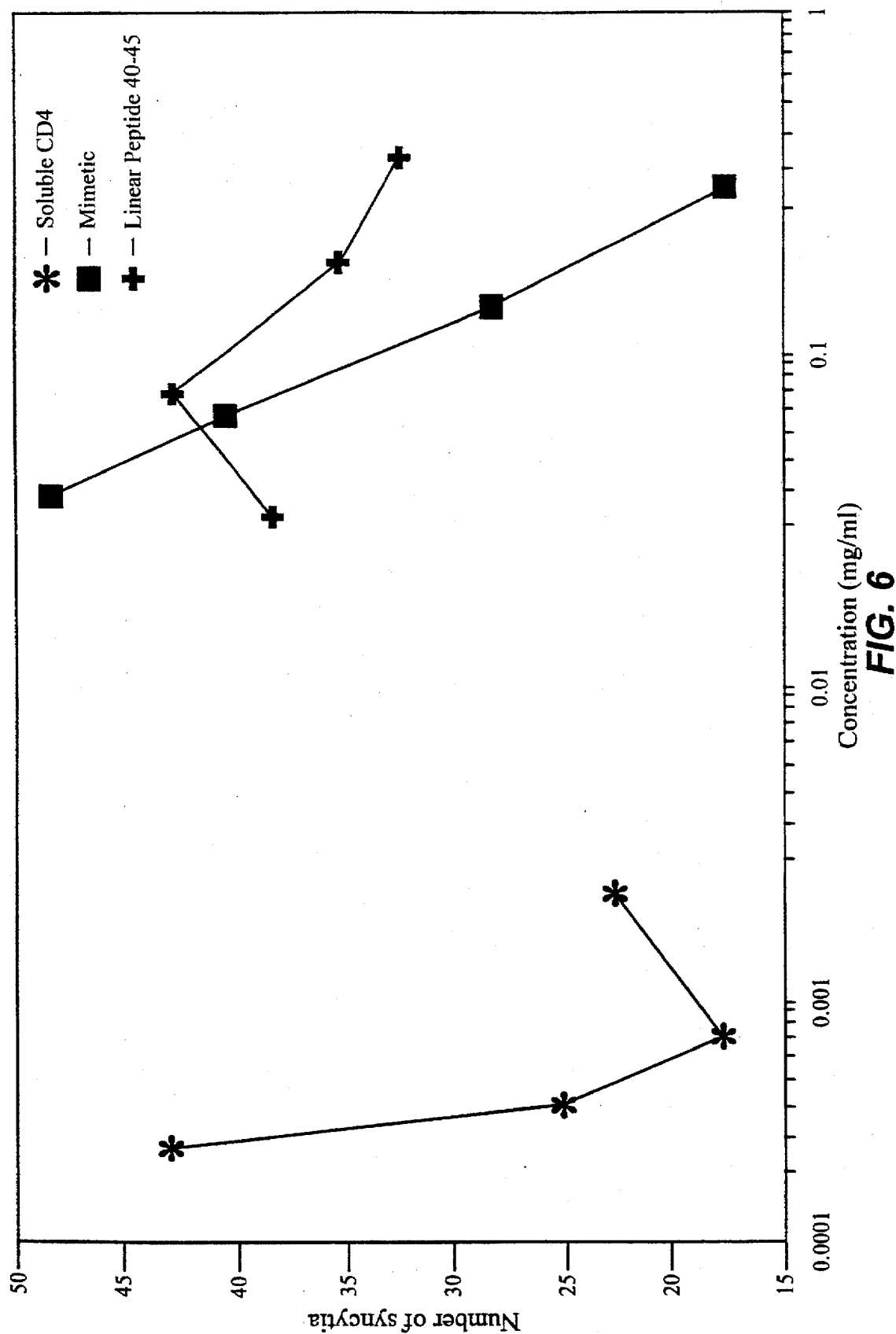
FIG. 6 is a summary of testing of the inhibition of syncytium formation by the mimetic of FIG. 5 (asterisks), soluble CD4 (squares), or CD4 hexapeptide of residues 40–45 (crosses).

Sup T1 cells (see Weiner et al., Pathobiology: 4:1–20 (1991)) were used as target cells for infection. Dilutions (1:2) of soluble CD4, CD4 mimetic, or CD4 peptide were made in 96 well plates in RPMI 1640 media containing 10% fetal calf serum. H9/IIIB infected cells were then plated at a density of approximately 10⁴ cells per well. Sup T1 target cells were then added (5×10⁵ per well) and syncytium formation was qualitatively and quantitatively determined after a 3 day incubation period. The results using soluble CD4, the reverse turn mimetic shown in FIG. 5, or the CD4 hexapeptide comprising residues 40–45 are shown in FIG. 6. The number of syncytia per well counted on visual inspection was plotted against the concentration of CD4, mimetic, or peptide added. The mimetic shown in FIG. 5 provided superior inhibition of syncytium formation.

EXAMPLE 15

This example details the liquid phase synthesis of a reverse turn mimetic of this invention. The synthesis is broken down into synthesis steps for easy understanding and the various chemical intermediates are given letter designations. The end product of the synthesis, intermediate product (N') has also been prepared using the solid phase synthesis techniques of this invention.

A. Third Modular Component Piece Synthesis
Step 1

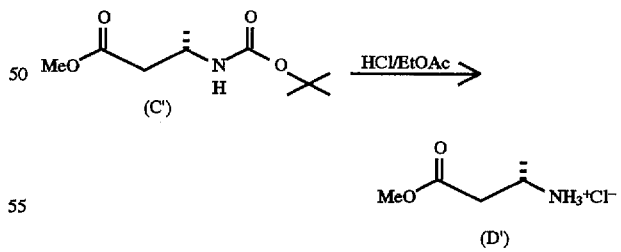

18.92 grams of 100 millimoles of BOC-alanine was dissolved in 80 ml of freshly distilled THF under a flame-dried argon atmosphere, The solution was cooled to 0° C. and at which point 14.29 ml (130 millimoles) of NMM was added to the solution. Next 16.86 ml (120 millimoles) of isobutyl chloroformate was dripped into the solution over the course of five minutes while the solution temperature was kept below 5° C. The solution was stirred at 0° C. for 90 minutes. The solids which evolved during the reaction were removed by vacuum filtration and washed with freshly distilled THF. The solids were placed in ether and 1 liter of a solution in ether containing 215 millimoles of CH$_2$N$_2$ was added and stirred at 0° C. for three hours. The volatile components of the solution were removed under reduced pressure to yield a crystalline yellow diazoketone shown as intermediate compound (B').

Step 2

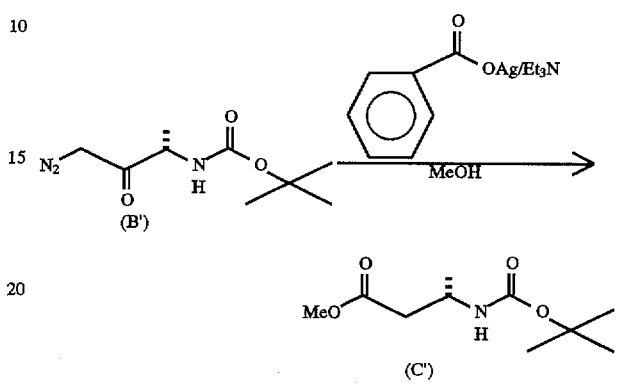

Twenty-four grams of intermediate compound (B') were dissolved in 80 ml of freshly distilled MeOH to produce a first solution. A second solution was prepared by dissolving 70 mg silver benzoate and 3 ml of methanol and thereafter 500 microliters of Et$_3$N was added to the second solution. The second silver benzoate solution was dripped into the first solution and the mixture was stirred for two hours. The volatiles were removed from the mixture under reduced pressure and the residue was dissolved in 400 ml CH$_2$Cl$_2$. The dissolved reactants were washed twice with 100 ml of a hydrochloric acid solution, twice with 100 ml of a saturated NaHCO$_3$ solution, with 100 ml of water and with 75 ml of saturated NaCl. The volatiles were removed from this solution under reduced pressure and the residue was dissolved in 200 ml EtOAc. The solution was treated with activated carbon, filtered, and the volatiles were removed under reduced pressure. The residue was crystallized from cold hexane yielding 17.3 grams of intermediate product (C').

Step 3

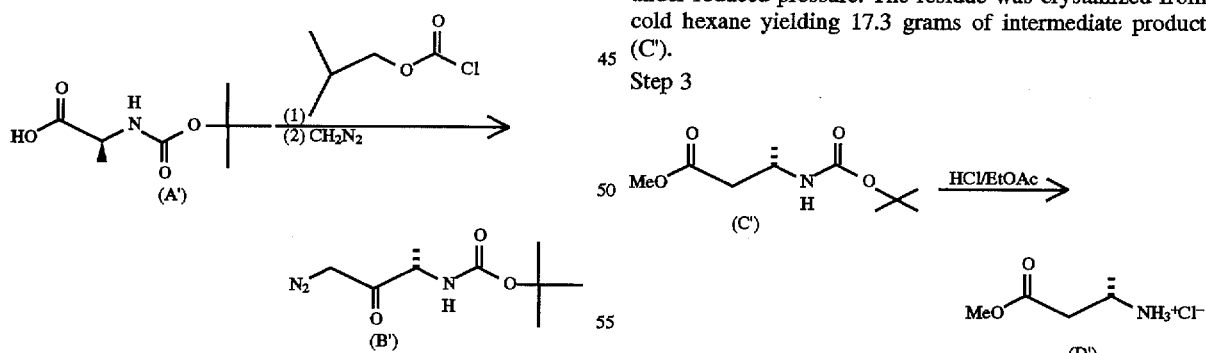

12.12 grams of intermediate product (C') was dissolved in 40 12.12 grams of intermediate product (C') was dissolved in 40 ml EtOAc under an argon atmosphere. The solution was cooled to 0° C. and 17 ml of a cold saturated HCl/EtOAc was added to the chilled solution. The mixture was stirred to room temperature. The volatiles were removed under reduced pressure and dried under high vacuum at approximately 40° C. for three hours resulting in intermediate product (D') a tan crystalline solid.

Step 4

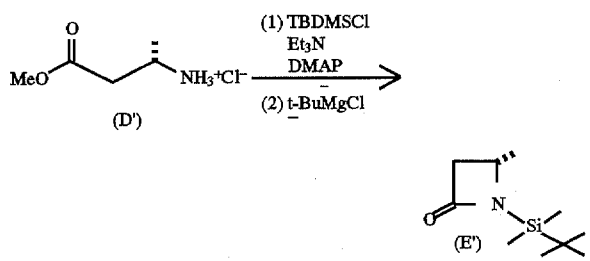

Intermediate product (D') was dissolved in 80 ml of freshly distilled $CH_2Cl_2$ under an argon atmosphere. 10.09 grams of TBDMSCl and 340 mg DMAP were added to the solution. Next, 18.68 ml of $Et_3N$ was slowly dripped into the stirred mixture. The resulting mixture was diluted to 600 ml with $CH_2Cl_2$ and quickly washed with 150 ml of saturated $NH_4Cl$, 150 ml of saturated $NaHCO_3$, and 100 ml of saturated NaCl. The solvent was removed under reduced pressure and the residue was azeotroped three times with 30 ml of freshly benzene water being careful not to allow the volume of the solution to drop below 15 ml. The residue was then dissolved in 350 ml of freshly distilled $Et_2O$ and cooled to 0° C. under an argon atmosphere. 48 ml of a two molar ether solution of t-BuMgCl was dripped into the solution and stirred overnight. The mixture was recooled to 0° C. and 10 ml of saturated $NH_4Cl$ was dripped into the mixture and the solution was stirred again at 0° C. for one hour. The solution was diluted to 700 ml with $Et_2O$ and washed twice with 150 ml of water and the combined aqueous layers were extracted with 300 ml of $Et_2O$. The combined organic layers were washed with saturated NaCl and then concentrated down to 20 ml. 200 ml of a 3%0 mixture of ethyl acetate-hexane was added to the 20 ml of concentrated solution and the mixture was filtered through a silica gel pad and the pad was washed with 100 ml of the 3%0 solution. The volatiles were removed to yield intermediate (E').

Step 5

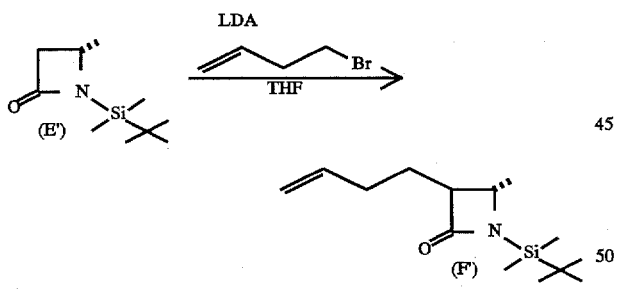

31.65 millimoles of LDA in solution was generated by dissolving 4.43 ml of freshly distilled diisopropylamine in 25 ml of freshly distilled THF under an argon atmosphere. The solution was cooled to 0° C. in an ice-bath at which point, 13.9 ml of a 2.5 molar n-BuLi solution in hexane was added to the chilled solution.

Intermediate product (E') was azeotroped three times with 20 ml volumes of freshly distilled benzene being careful not to lower the volume of the solution below 5 ml. The solution was placed in an argon atmosphere and 10 ml of freshly distilled THF was added to the residual solution.

The LDA solution prepared above was cooled to −78° C. and added to the azeotroped solution containing intermediate product E and stirred at −78° C. for 30 minutes. 2.78 ml of 4-bromo-1-butene was dripped into the solution and stirred at −78° C. for three hours. The mixture was kept at −4° C. overnight. The reaction was quenched with saturated $NH_4Cl$ and diluted to 500 ml with $Et_2O$. The diluted solution was washed with 75 ml of water, 75 ml of brine and then dried over $Na_2SO_4$. The volatiles removed from the solution under reduced pressure and the residue was separated chromatographically using a 10% solution of ethyl acetate in hexane as the mobile phase to yield intermediate product (F').

Step 6

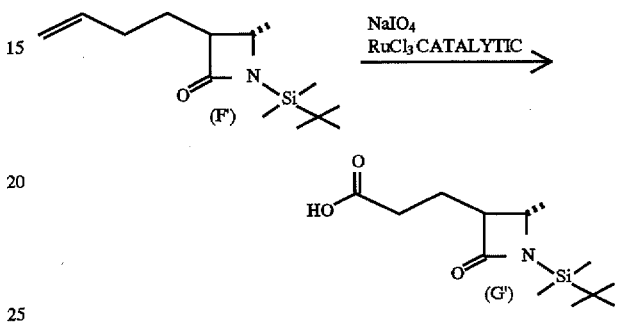

Intermediate product (F') was dissolved in 3 ml of carbon tetrachloride, 3 ml of AcCN and 6 ml of water. 75 mg of $RuCl_3$ and 6.64 grams of $NaIO_4$ were added to the solution and stirred overnight. The solution was partitioned between 300 ml of EtOAc and 200 ml of brine. One gram of NaCl was added to the solution and the mixture was stirred for two hours. The layers were allowed to separate and the aqueous layer was extracted twice with 200 ml of EtOAc. The combined organic layers were washed with brine and dried over $Na_2SO_4$ and thereafter concentrated down to approximately 2 grams of a dark filmy oil. The oil was dissolved in 10 ml of EtOAc and filtered through celite. The filtrate was concentrated down to approximately two grams of a clear tan oil which solidified to a waxy crystalline solid overnight. The clear tan oil is intermediate product (G').

B. Mixed Anhydride Coupling

Step 7

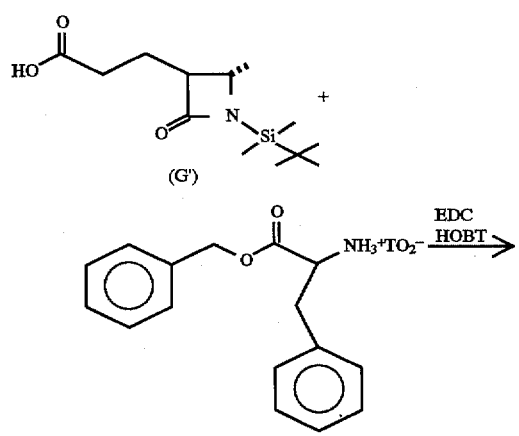

C. Liquid Phase Silver Cyanide Coupling

Step 9

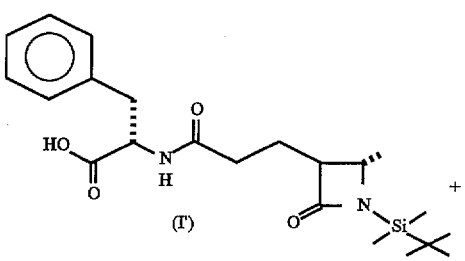

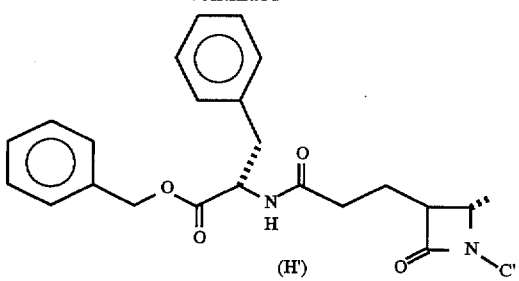

Intermediate product (G') and 2.9 grams of L-phenylanine benzylester was dissolved in 10 ml of THF/H$_2$O (4:1). 916 mg of HOBT and 1 ml Et$_3$N were dissolved in 15 ml of freshly distilled CH$_2$Cl$_2$ all under an argon atmosphere. The mixture was cooled to 0° C. in an ice-bath and 1.95 grams of EDC was added to the solution and the reaction was stirred overnight. The solution was diluted to 400 ml with CH$_2$Cl$_2$ and washed once with 100 ml of water, twice with 100 ml of saturated NH$_4$Cl, once with 100 ml of NaHCO$_3$, once with 100 ml of water and once with 75 ml of saturated NaCl. The washed solution was dried over Na$_2$SO$_4$ and the volatiles were removed under reduced pressure. The residue was dried under high vacuum overnight to yield intermediate product (H'), a greenish oil.

Step 8

Intermediate product (H') was dissolved in 50 ml of methanol and 30 mg of 5% PdC was added to the solution. The solution was shaken for 12 hours under a 50 psi hydrogen atmosphere. The solution was then filtered through celite, concentrated, and dried at high vacuum overnight to yield intermediate product (I'), a clear oil consisting of a second and third modular component piece of this invention.

Intermediate product (I') was azeotroped three times with 25 ml of freshly distilled benzene and dissolved in 18 ml of freshly distilled CH$_2$Cl$_2$ under an argon atmosphere. The solution was cooled to −15° G at which point, 410 microliters of pyridine was added to the solution followed by 1.38 ml cyanuric fluoride. The mixture was stirred at −15° C. for 2½ hours during which time solids formed in the solution. The solution was diluted to approximately 40 ml with cold CH$_2$Cl$_2$ and crushed ice was added and stirred for five minutes. The solution was partitioned between 100 ml of ice cold CH$_2$Cl$_2$ and 30 ml of cold water. The organic layer was washed with 30 ml of ice cold brine and dried over magnesium sulfate. The solvent was removed under reduced pressure at room temperature. The residue was dried at high vacuum for 15 minutes.

The residue was then placed under an argon atmosphere and 1.24 grams of first modular component J was added to the residue along with 1.45 grams (10.9 millimoles) of AgCN. 20 ml of freshly distilled benzene was added to the mixture and stirred vigorously at 50° C. for two hours. The solution was stirred overnight filtered through a celite pad after which volatiles were removed under reduced pressure to yield intermediate product (K'), a light brown oil.

25

D. Deprotecting and Cyclization

Step 10

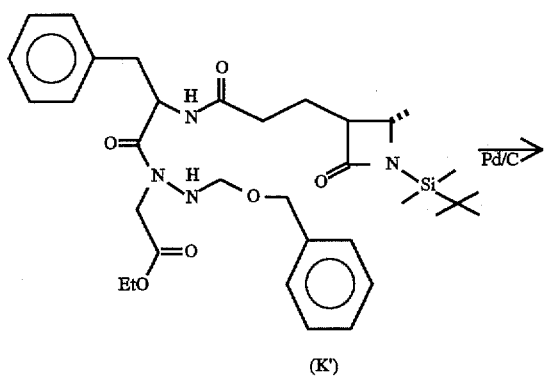

(K')

Intermediate product (K') was dissolved in 50 ml of absolute EtOH placed in a shaker bottle and 200 mg of 5% Pd/C was added to the solution. The solution was shaken overnight under a 50 psi hydrogen atmosphere. The shaken solution was then filtered through a celite pad and the volatiles removed under reduced pressure to yield intermediate product (L').

Step 11

(L')

26

(M')

40 mg of intermediate product (L') was dissolved in 2 ml. THF. 73 mg (231 micromoles 3 eq) TBAF·3H$_2$O was added to the mixture and the entire mixture was stirred for 45 minutes. The volatiles were removed from the solution under reduced pressure to yield a yellow oil. The product was chromatographed over flash grade silica gel using 3% MeOH in CH$_2$Cl$_2$ as the mobile phase to yield intermediate M', a clear oil.

F. Reverse Turn Intermediate Synthesis.

(N')

60 mg of intermediate product (M') was mixed with 95 mg (192 micromoles, 1.3 eq.) FMOC-Tyr acid fluoride, 103 mg (768 micromoles, 4 eq of AgCN in a 10 ml. rb with a reflux condenser under an argon atmosphere. The mixture was dried under high vacuum at 40° C. for 6 hours. 4.5 ml of freshly distilled benzene was added to the mixture under an argon atmosphere and the mixture was heated at gentle reflux for 24 hours, and then filtered through a ⁵⁰/₅₀ celite/ silica gel pad and washed with EtOAc. The volatiles were removed yielding a tan oily product (N').

Product (N'), above, was submitted for pharmacological studies. The compound bound to gamma opioid receptors at micromolar levels and produced antinociception at 10 micrograms/g IGV in mice.

EXAMPLE 16

Solid Phase Acid Fluoride Coupling

Figure 1A:
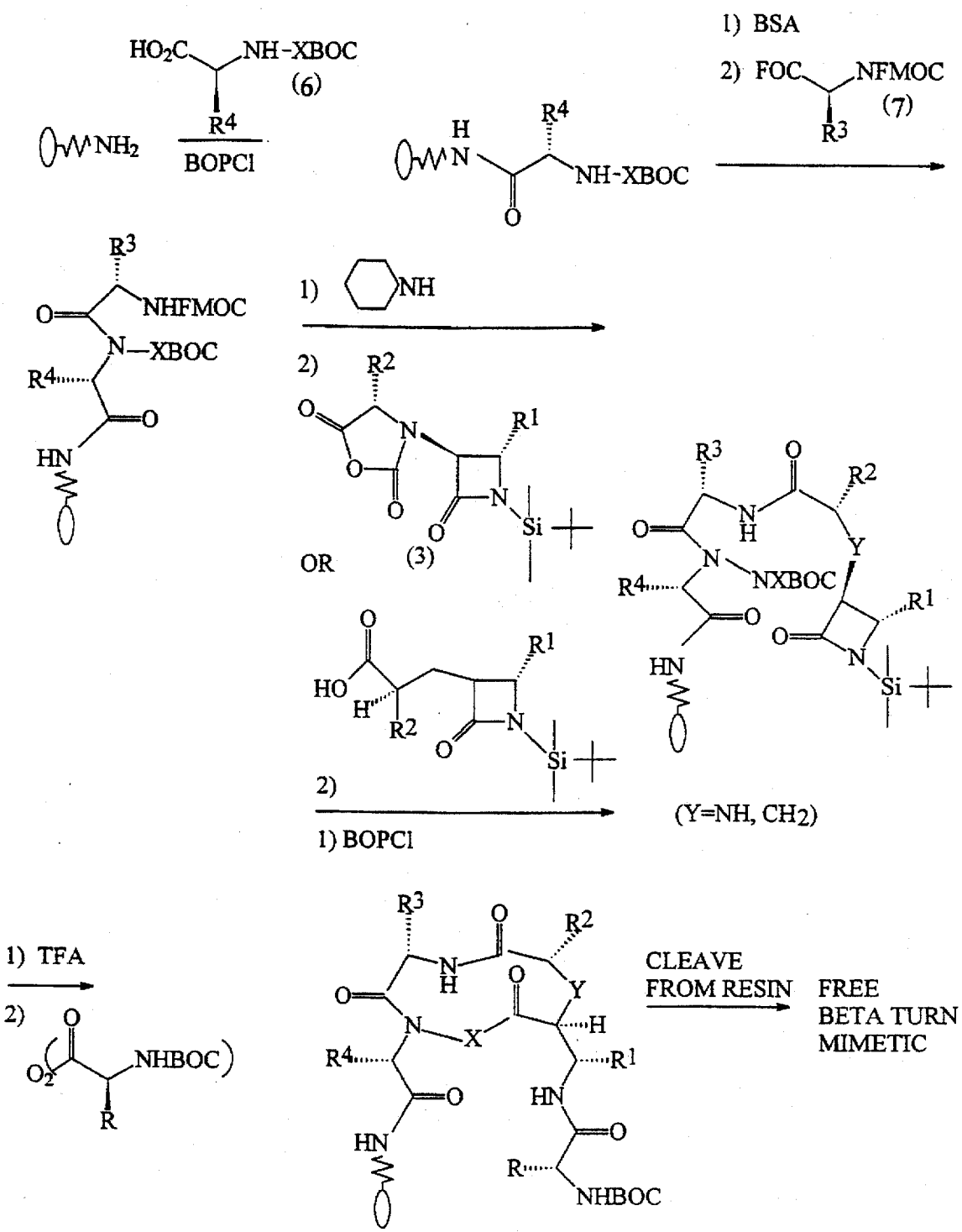

The preparation of a support-bound reverse turn mimetic is detailed in FIG. 1A. Solid phase synthesis was carried out on an Advanced Chemtech 200 synthesizer using standard protocols described in Stewart, J. M. and Young, J. D. (1984) Solid Phase Peptide Synthesis, 2nd Ed. Pierce Chemical Co., Rockford, Ill. Protected amino acids were generally incorporated by double couplings of their respective symmetrical anhydrides.

The silicon mediated acid fluoride coupling step of the solid phase synthesis method of this invention is performed as follows:

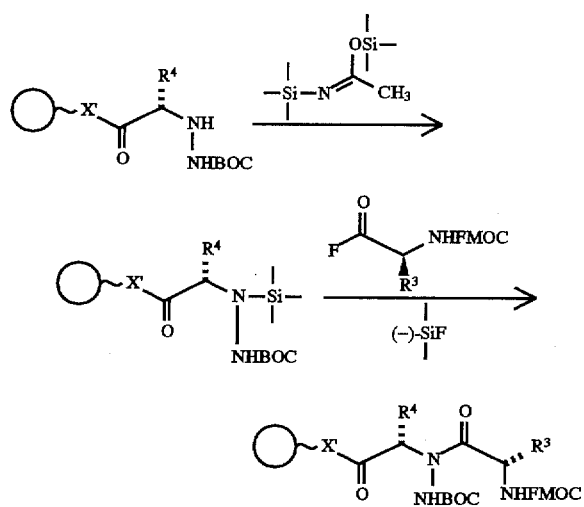

After coupling the first modular component piece, the resin is reacted with 5eq of bis-trimethylsilyl acetamide as a solution in THF for 15 minutes. The resulting resin is washed with THF. A solution of acid fluoride in THF was then prepared according to the method of Carpino and Han, JACS 1990, (9651–52) and is added to the resin solution and the resulting reaction is allowed to proceed until it is complete as judged by the Kaiser ninhydrin assay. This solid phase acid fluoride coupling procedure provides nearly quantitative acylation of the hydrazine nitrogen whereas all other coupling procedures attempted provide, at best, less than 20% acylation after exhaustive coupling.

The resin is attached to the X⁻ component of a first modular component. X⁻ may be selected from the group NH and O. Additionally, the selection of protective group, e.g., FMOC of BOC is not critical to the synthesis method.

EXAMPLE 17

It is believed that the HIV gp120 V3 loop, which comprises the PND (principal neutralizing determinant) can exist in one of the following two reverse turn conformations.

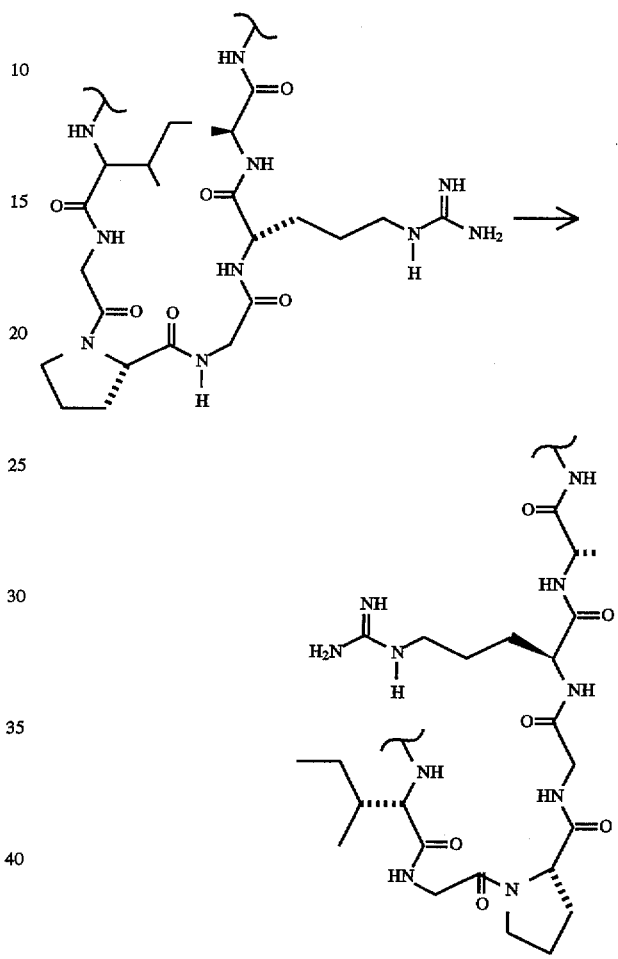

Conformationally restricted beta turn mimetics were synthesized having the structures below.

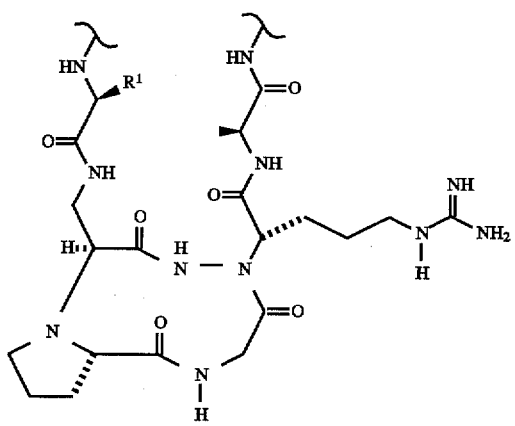

-continued

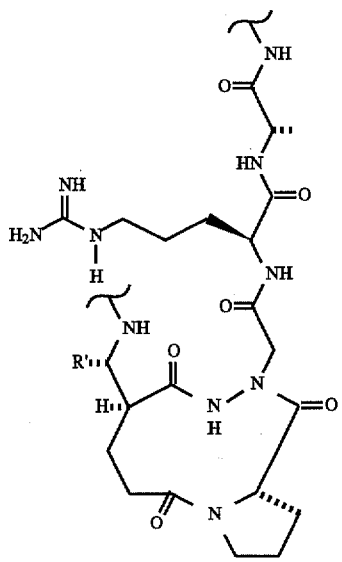

wherein R' is

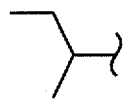

or

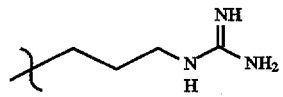

The following compound (3) was synthesized using solid phase peptide synthesis techniques outlined in Example 16.

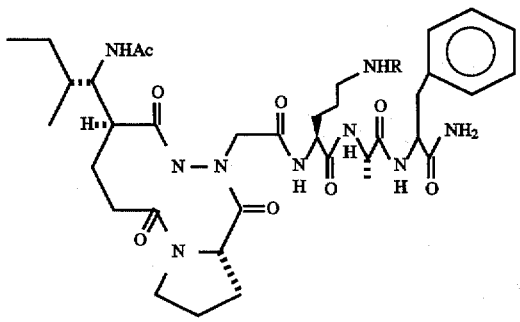

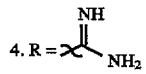

The compound was then guanidylated with

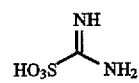

in methanol with NaHCO$_3$ to produce compound (4). Similar strategies can be used to synthesize conformationally restricted immunogens with a range of N and C terminal extensions.

I claim:

1. A beta-hairpin mimetic having the structure:

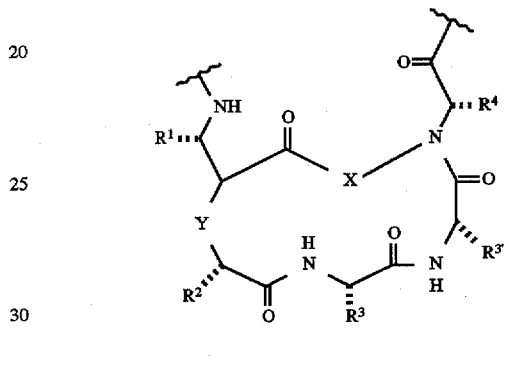

or

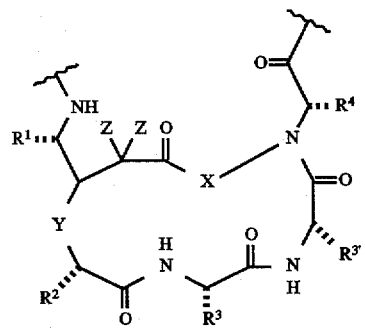

wherein X is a linker moiety; Y is selected from —CH$_2$—, —NH— and —N(CH$_3$)—; Z is hydrogen or methyl; and R$^1$, R$^2$, R$^{3'}$ and R$^4$ are individually selected from naturally occurring amino acid side chain substituents.

2. The beta-hairpin mimetic of claim 1 having the structure:

3. The beta-hairpin mimetic of claim 1 having the structure:

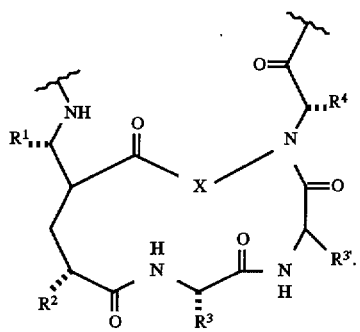

4. The beta-hairpin mimetic of claim 1 having the structure:

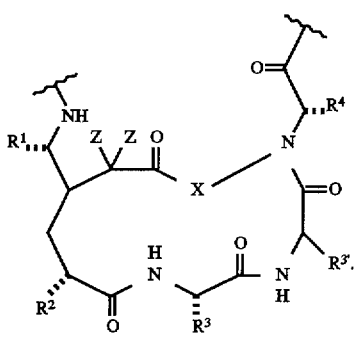

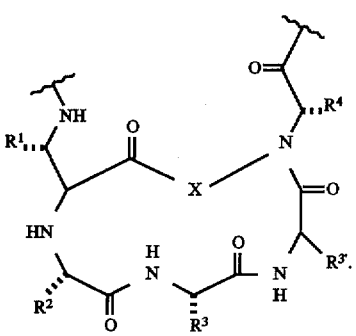

5. The beta-hairpin mimetic of claim 1 having the structure:

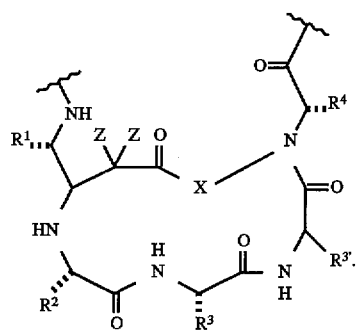

6. A beta-hairpin mimetic having the structure:

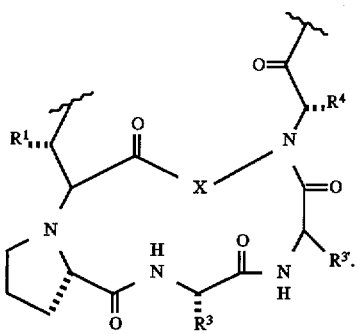

wherein X is a linker moiety; and $R^1$, $R^3$, $R^{3'}$ and $R^4$ are selected from naturally occuring amino acid side chain substituents.

7. The beta-hairpin mimetic of any one of claims 1–6 wherein X is selected from —$(CH_2)_n$NH—, —$(CH_2)_n$C(R)(R')NH— and —CH=CH$(CH_2)_n$NH—, where n=0–4 and R and R' are individually selected from —H and —$CH_3$.

* * * * *